US005306692A

United States Patent [19]

Barton et al.

[11] Patent Number: 5,306,692

[45] Date of Patent: Apr. 26, 1994

[54] HERBICIDAL INDAZOLE AND BENZIMIDAZOLE COMPOUNDS

[75] Inventors: John E. D. Barton; David Cartwright, both of Reading; Derek McCormack, Windsor, all of England

[73] Assignee: Zeneca Limited, London, United Kingdom

[21] Appl. No.: 652,337

[22] Filed: Feb. 7, 1991

[30] Foreign Application Priority Data

| | | | |
|---|---|---|---|
| Feb. 16, 1990 | [GB] | United Kingdom | 9003548 |
| Feb. 16, 1990 | [GB] | United Kingdom | 9003549 |
| Aug. 2, 1990 | [GB] | United Kingdom | 9016979 |
| Nov. 5, 1990 | [GB] | United Kingdom | 9023984 |
| Dec. 10, 1990 | [GB] | United Kingdom | 9026810 |

[51] Int. Cl.[5] .................. C07D 213/30; C07D 235/26; A01N 43/50; A01N 43/56

[52] U.S. Cl. .................................... 504/139; 504/130; 546/271; 548/306.4; 548/308.7; 548/361.5; 548/362.1; 548/362.5

[58] Field of Search ..................... 548/373, 375, 306.4, 548/362.1; 71/92; 504/139, 130; 546/270, 271

[56] References Cited

U.S. PATENT DOCUMENTS 3,637,736 1/1972 Minieri .................................... 71/94

FOREIGN PATENT DOCUMENTS

| | | | |
|---|---|---|---|
| 104727 | 4/1984 | European Pat. Off. | 71/92 |
| 178708 | 4/1986 | European Pat. Off. | |
| 238266 | 9/1987 | European Pat. Off. | |
| 299446 | 1/1989 | European Pat. Off. | |
| 1580215 | 9/1969 | France | 71/92 |
| 59-98060 | 6/1984 | Japan | |
| 1213796 | 11/1970 | United Kingdom | 71/92 |
| 2157679 | 10/1985 | United Kingdom | |

*Primary Examiner*—Floyd D. Higel
*Attorney, Agent, or Firm*—Joel G. Ackerman

[57] ABSTRACT

A herbicidal compound of formula (I):

Ar—W—[benzo ring fused to five-membered ring A, B, D] (I)

or N-oxide or quaternised derivative thereof;

Ar is an optionally substituted aryl or heterocyclic ring system;

W is O or $NR^1$ where $R^1$ is H or lower alkyl;

A, B, D are independently selected from N, $NR^2$, N—E, $CR^6$, C—E or $C(R^6)E$;

wherein E is:

$$-C(R^3)(R^4)-XR^5;$$

provided 2 of A, B and D are N, $NR^2$ or N—E;

one of A, B and D is $CR^6$, C—E or $C(R^6)$ E and at least one of A, B or D carries a group E;

where $R^2$ is H, $OR^7$, CN, $COOR^8$, alkyl or haloalkyl;

$R^3$ and $R^4$ are independently selected from H, optionally substituted alkyl, alkenyl or alkynyl, halogen, $NR^9R^{10}$, or $R^3$ and $R^4$ together with the carbon to which they are attached form an optically substituted alkenyl or cycloalkyl group:

X is $(CH_2)_n$, CH=CH, $CH(OR^{16})CH_2$ or $COCH_2$ where n is O, 1 or 2;

$R^5$ is $CO_2R^{11}$, CN, $COR^{11}$, $CH(OH)R^{11}$, $CH(OR^{11})R^{12}$, $CSNH_2$, $COSR^{11}$, $CSOR^{11}$, $CONHSO_2R^{11}$, $CONR^{13}R^{14}$, $CONHNR^{13}R^{14}R^{15}$ $Y^-$, $CO_2^-M^+$ or $COON{=}CR^{13}R^{14}$;

$R^6$ is H, halogen, $OR^7$, CN, $COOR^8$, alkyl or haloalkyl; and $R^7$, $R^8$, $R^9$, $R^{10}$, $R^{11}$, $R^{12}$, $R^{13}$, $R^{14}$, $R^{15}$ and $R^{16}$ are specified organic groups.

8 Claims, No Drawings

HERBICIDAL INDAZOLE AND BENZIMIDAZOLE COMPOUNDS

The present invention relates to novel substituted benzimidazole and indazole derivatives, processes for their preparation, their use as herbicides and herbicidal compositions containing them.

European Patent No. 178,708 A describes certain benzheterocyclic-phenyl ether derivatives which have herbicidal activity.

Japanese Patent Kokai No. 59-98060 describes certain indazole derivatives.

According to the present invention there is provided a compound of formula (I):

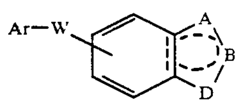

(I)

or N-oxide or quaternised derivative thereof;

in which the dotted lines indicate the presence of two double bonds arranged so as to form a fused hetero-aromatic ring system;

Ar is an optionally substituted aryl or heterocyclic ring system;

W is O or $NR^1$ where $R^1$ is H or lower alkyl;

A, B, D are independently selected from N, $NR^2$, N—E, $CR^6$,

C—E or $C(R^6)E$;

wherein E is:

$$\begin{array}{c} Z \\ | \\ R^3—C—R^4 \\ | \\ XR^5 \end{array} \qquad (VII)$$

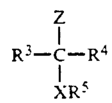

provided 2 of A, B and D are N, $NR^2$ or N—E and at least one of A, B or D carries a group E;

where $R^2$ is H, $OR^7$, CN, $COOR^8$, alkyl or haloalkyl;

$R^3$ and $R^4$ are independently selected from H, optionally substituted alkyl, alkenyl or alkynyl, halogen, $NR^9R^{10}$ or $R^3$ and $R^4$ together with the carbon to which they are attached form an optionally substituted alkenyl or cycloalkyl group;

$R^5$ is $CO_2R^{11}$, CN, $COR^{11}$, $CH_2OR^{11}$, $CH(OH)R^{11}$, $CH(OR^{11})R^{12}$, $CSNH_2$, $COSR^{11}$, $CSOR^{11}$, $CONHSO_2R^{11}$, $CONR^{13}R^{14}$, $CONHNR^{13}R^{14}$, $CONHN^+R^{13}R^{14}R^{15}$ $Y^-$, $CO_2^-M^+$ or $COON{=}CR^{13}R^{14}$;

X is $(CH_2)_n$, CH=CH, $CH(OR^{16})CH_2$ or $COCH_2$;

where n is O, 1 or 2;

$M^+$ is an agriculturally acceptable cation;

$Y^-$ is an agriculturally acceptable anion;

$R^6$ is H, halogen, $OR^7$, CN, $COOR^8$, alkyl or haloalkyl;

$R^7$ and $R^8$ are independently H or lower alkyl;

$R^{11}$, $R^{12}$ and $R^{16}$ are independently selected from H or an optionally substituted alkyl, alkenyl, alkynyl or aryl group; and $R^9$ $R^{10}$, $R^{13}$, $R^{14}$ and $R^{15}$ are independently selected from H or an optionally substituted alkyl, alkenyl, alkynyl or aryl group or any two of $R^9$, $R^{10}$, $R^{13}$, $R^{14}$ and $R^{15}$ together with the atom to which they are attached form a cycloalkyl or heterocyclic ring providing that the compound is other than 5-(2,4-dichlorophenoxy)indazol-1-ylacetic acid or its methyl ester.

Quaternised derivatives of compounds of formula (I) are compounds obtained by reacting a compound of formula (I) with a quaternising agent such as an alkyl halide or a trialkyloxonium species. It is believed that such quaternised derivatives carry a charge on a single nitrogen atom, and this is on an $NR^2$ group within the molecule in preference to an N—E group. For example, where A is $NR^2$, B is $CR^6$ and D is $NCR^3R^4XR^5$, the quaternised derivative is believed to have the formula:

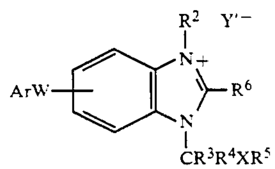

where Ar, W, $R^2$, $R^3$, $R^4$, $R^5$, $R^6$ and X are as defined in relation to formula (I) and $Y'^-$ is an anion derived from the quaternising agent such as a halide, tetrafluoroborate, mesylate or tosylate ion.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "cycloalkyl" includes rings containing from 3 to 9 carbon atoms, preferably from 3 to 6 carbon atoms. The term "alkoxy" includes straight or branched chains containing up to 10 carbon atoms preferably from 1 to 6 carbon atoms.

The term "lower" used in relation to alkyl, alkoxy, alkenyl or alkynyl groups means that the group contains up to 3 carbon atoms.

The term "haloalkyl" and "haloalkoxy" refer to alkyl and alkoxy groups respectively substituted by at least one halogen atom such as fluorine, chlorine or bromine. A particular haloalkyl group is trifluoromethyl. The term "aryl" includes phenyl and naphthyl. The term "heterocyclic" includes rings of up to 10 atoms, preferably up to 6 atoms up to 3 of which are selected from oxygen, nitrogen or sulphur. The term halogen includes fluorine, chlorine, bromine and iodine.

A suitable aryl ring system is phenyl.

Suitable heterocyclic ring systems for Ar are rings of up to 10 atoms, up to 3 of which are selected from oxygen, nitrogen or sulphur, preferably aromatic ring systems such as pyridine and pyrazole.

Suitable optional substitutents for the aryl or heterocyclic ring systems Ar and for the aryl groups $R^9$, $R^{10}$, $R^{11}$, $R^{12}$, $R^{13}$, $R^{14}$, $R^{15}$ and $R^{16}$ are up to 5 preferably up to 3 members selected from halogen (fluoro, chloro, bromo or iodo), lower alkyl, haloalkyl (for example $CF_3$), haloalkoxy (for example $OCF_3$), nitro, cyano, lower alkoxy (for example methoxy) or $S(O)_pR^a$ a where p is 0, 1 or 2 and $R^a$ is alkyl (for example thiomethyl, sulphinylmethyl and sulphonylmethyl).

Preferred positions of substitution when the aryl ring is a phenyl ring are the 2, 4 and 6 positions, particularly 2,4,6-tri- substituted rings with a trifluoromethyl group at the 4-position.

Examples of optional substituents for alkyl, alkenyl, alkynyl groups $R^3$, $R^4$, $R^9$, $R^{10}$, $R^{11}$, $R^{12}$, $R^{13}$, $R^{14}$, $R^{15}$ and $R^{16}$ and include one or more groups selected from halo such as fluoro, chloro or bromo; nitro; cyano; aryl such as phenyl; $CO_2R^{17}$, $NHCOR^{17}$ or $NHCH_2CO_2R^{17}$ wherein $R^{17}$ is hydrogen, $C_{1-6}$ alkyl or an agriculturally acceptable cation; $C_{1-6}$ alkoxy; oxo; $S(O)_pR^a$ where p is 0, 1 or 2 and $R^a$ is alkyl (for example thiomethyl, sulphinylmethyl and sulphonylmethyl); amino; mono- or di- $C_{1-6}$ alkylamino; $CONR^{18}R^{19}$ wherein $R^{18}$ and $R^{19}$ are independently selected from hydrogen, $C_{1-6}$ alkyl, $C_{2-6}$ alkenyl or $C_{2-6}$ alkynyl or $R^{18}$ and $R^{19}$ are joined together to form a heterocyclic ring having up to 7 ring atoms 3 of which may be selected from oxygen, nitrogen or sulphur. An example of a heterocyclic substitutent is tetrahydrofuranyl.

Examples of agriculturally acceptable anions for $Y^-$ are halides, tetrafluoroborate, mesylate and tosylate.

Examples of agriculturally acceptable cations for $R^{17}$ and $M^+$ are sodium, potassium or calcium ions, sulphonium or sulphoxonium ions for example of formula $S^+(O)_qR^9R^{10}R^{13}$ where q is 0, or 1 and $R^9$, $R^{10}$ and $R^{13}$ are as hereinbefore defined or ammonium or tertiary ammonium ions of formula $N^+R^9R^{10}R^{13}R^{14}$ where $R^9$, $R^{10}$, $R^{13}$ and $R^{14}$ are as hereinbefore defined. Suitable substituents for the alkyl, alkenyl and alkynyl groups in these cations are hydroxy and phenyl. Suitably where any of $R^9$, $R^{10}$, $R^{13}$ and $R^{14}$ in these cations are optionally substituted alkyl, they contain from 1 to 4 carbon atoms.

Particular examples of $R^9$, $R^{10}$, $R^{13}$ and $R^{14}$ in these cations are hydrogen, ethyl, isopropyl, benzyl, and 2-hydroxyethyl.

Suitable halo groups $R^3$, $R^6$, and $R^{14}$ include fluorine, chlorine and bromine.

Suitable heterocyclic rings formed from two of $R^9$, $R^{10}$, $R^{13}$, $R^{14}$ and $R^{15}$ and the atom to which they are attached are pyrrolidine, piperidine and morpholine.

Suitable groups of sub-formula (i):

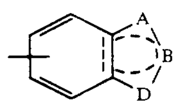

(i)

are the following groups:

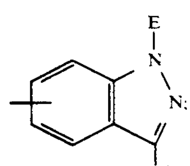

(a)

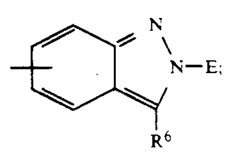

(b)

-continued

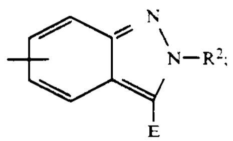

(c)

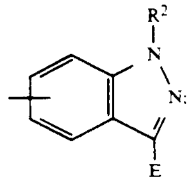

(d)

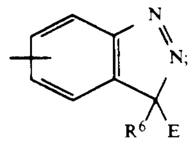

(e)

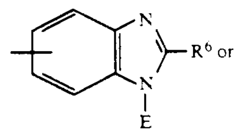

(f)

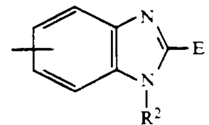

(g)

Preferably the group of sub-formula (i) is group (a) or (f) as defined above.

Preferably $R^3$ is H.

Preferably $R^4$ is H or is $C_{1-3}$ alkyl, in particular methyl.

Suitably $R^5$ is $CO_2R^{11}$, $CONR^{13}R^{14}$, $CONHSO_2R^{11}$, $COON{=}CR^{13}R^{14}$, $CONHNR^{13}R^{14}$ or $CONHN^+R^{13}R^{14}R^{15}\,Y^-$.

Preferably $R^5$ is $CO_2R^{11}$.

$R^{11}$ is suitably $C_{1-6}$ alkyl or substituted alkyl such as alkoxyalkyl or oxo substituted alkyl.

Preferably R11 is methyl or ethyl.

Ar is preferably a group:

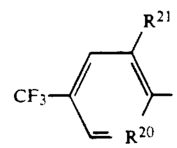

where $R^{20}$ is N, CH or $CR^{22}$; $R^{22}$ and $R^{22}$ are independently selected from halogen such as chlorine or fluorine.

Preferably $R^{20}$ is $CR^{22}$ and most preferably one of $R^{21}$ and $R^{22}$ is chlorine and the other is fluorine.

W is preferably oxygen.

Preferably X is $(CH_2)_n$ where n is zero or 1, especially zero.

When the group of sub-formula (i) is group (a) above, $R^6$ is preferably H or Cl.

When the group of sub-formula (i) is group (f) above, $R^6$ is preferably H, $CH_3$, $CF_3$ or CN.

An example of a sub-group of formula (I) are compounds of formula (IA):

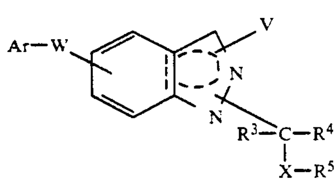

in which the dotted lines indicate the presence of two double bonds arranged so as to form a fused hetero-aromatic ring system;

Ar, W, X, $R^3$, $R^4$ and $R^5$ are as defined in relation to formula (I) and

V is H, halogen, $OR^7$, CN, $COOR^8$, alkyl or haloalkyl provided that when V is halogen it is not attached to a nitrogen atom and further provided that the compound is other than 5-(2,4-dichlorophenoxy)indazol-1-ylacetic acid or its methyl ester.

A further example of a sub-group of formula (I) are compounds of formula (IC):

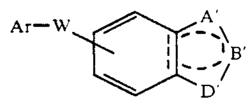

or a quaternised derivative thereof;

in which

Ar and W are as defined in relation to formula (I) and

A' is N, NH or N-lower alkyl;

B' is C—$R^6$ or C—E;

D' is N—E, NH or N-lower alkyl provided that when B' is C—$R^6$, D' is not NH or N-lower alkyl; and E and $R^6$ are as defined in relation to formula (I).

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Some of the compounds of the invention can exist in enantiomeric forms. The invention includes both individual enantiomers and mixtures of the two in all proportions.

Particular examples of compounds according to the invention are listed in Tables I, II, III, IV and V. Characterizing data for the compounds are given in Table VI.

TABLE I

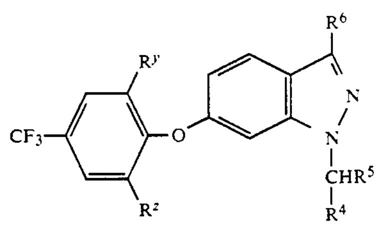

| Compound No | $R^y$ | $R^z$ | $R^4$ | $R^5$ | $R^6$ |
|---|---|---|---|---|---|
| 1 | F | Cl | $CH_3$ | $CO_2C_2H_5$ | H |
| 2 | F | Cl | H | $CO_2C_2H_5$ | H |
| 3 | F | Cl | $CH_3$ | $CO_2H$ | H |
| 4 | F | Cl | H | $CO_2H$ | H |
| 5 | F | Cl | H | $CO_2CH_3$ | H |
| 6 | Cl | Cl | $CH_3$ | $CO_2C_2H_5$ | H |
| 7 | H | $NO_2$ | $CH_3$ | $CO_2C_2H_5$ | H |
| 8 | H | CN | $CH_3$ | $CO_2C_2H_5$ | H |
| 9 | H | Cl | $CH_3$ | $CO_2C_2H_5$ | H |
| 10 | F | Cl | $CH_3$ | $CO_2CH_3$ | H |
| 11 | F | Cl | $CH_3$ | $CO_2nPr$ | H |
| 12 | F | Cl | $CH_3$ | $CO_2nBu$ | H |
| 13 | F | Cl | $CH_3$ | $CO_2C_2H_5$ | Cl |
| 14 | CN | Cl | $CH_3$ | $CO_2C_2H_5$ | H |
| 15 | $NO_2$ | Cl | $CH_3$ | $CO_2C_2H_5$ | Cl |
| 16 | CN | Br | $CH_3$ | $CO_2C_2H_5$ | Cl |
| 17 | $NO_2$ | $NO_2$ | $CH_3$ | $CO_2C_2H_5$ | Cl |
| 19 | F | Cl | $CH_3$ | $CONH_2$ | Cl |
| 20 | F | Cl | $CH_3$ | $CONH\overset{+}{N}(CH_3)_3\overset{-}{I}$ | Cl |
| 21 | H | Cl | H | $CO_2C_2H_5$ | H |
| 22 | H | $NO_2$ | H | $CO_2C_2H_5$ | Cl |
| 23 | H | CN | H | $CO_2C_2H_5$ | Cl |
| 24 | H | Cl | H | $CO_2C_2H_5$ | Cl |
| 25 | H | $NO_2$ | H | $CO_2C_2H_5$ | Cl |
| 26 | H | CN | H | $CO_2C_2H_5$ | Cl |
| 27 | F | Cl | H | $CO_2H$ | Cl |
| 28 | F | Cl | H | $CO_2CH_3$ | Cl |
| 29 | F | Cl | H | $CO_2nPr$ | Cl |
| 30 | F | Cl | H | $CO_2nBu$ | Cl |
| 31 | F | Cl | H | $CO_2C_2H_5$ | Cl |
| 32 | F | Cl | $CH_3$ | $CONHN(CH_3)_2$ | H |
| 40 | F | Cl | $CH_3$ | $CO_2H$ | Cl |
| 41 | F | Cl | $CH_3$ | $CO_2^-Na^+$ | H |
| 42 | F | Cl | $CH_3$ | $CO_2CH_3$ | Cl |
| 43 | F | Cl | $CH_3$ | $CO_2iPr$ | Cl |
| 44 | F | Cl | $CH_3$ | $CO_2nBu$ | Cl |
| 45 | F | Cl | $CH_3$ | $CO_2nPr$ | Cl |
| 46 | F | Cl | $CH_3$ | $CO_2(CH_2)_2OCH_3$ | Cl |
| 47 | F | Cl | $CH_3$ | $CO_2N{=}C(CH_3)_2$ | Cl |
| 48 | Cl | Cl | $CH_3$ | $CO_2C_2H_5$ | Cl |
| 49 | H | CN | $CH_3$ | $CO_2C_2H_5$ | Cl |
| 50 | Cl | CN | $CH_3$ | $CO_2C_2H_5$ | Cl |
| 51 | F | Cl | $CH_3$ | $CO_2$–$C_6H_4$–$NO_2$ | H |
| 52 | F | Cl | $CH_3$ | $CO_2N{=}C(CH_3)_2$ | H |
| 53 | Cl | Cl | $CH_3$ | $CO_2H$ | Cl |
| 54 | H | CN | $CH_3$ | $CO_2H$ | Cl |
| 55 | Cl | CN | $CH_3$ | $CO_2H$ | Cl |

TABLE II

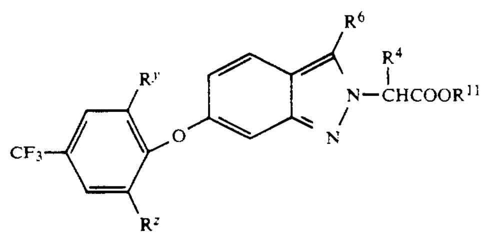

| Compound No | $R^y$ | $R^z$ | $R^4$ | $R^{11}$ | $R^6$ |
|---|---|---|---|---|---|
| 33 | F | Cl | $CH_3$ | $C_2H_5$ | H |
| 34 | F | Cl | H | $C_2H_5$ | H |
| 35 | F | Cl | $CH_3$ | $CH_3$ | H |
| 36 | F | Cl | $CH_3$ | H | H |

TABLE III

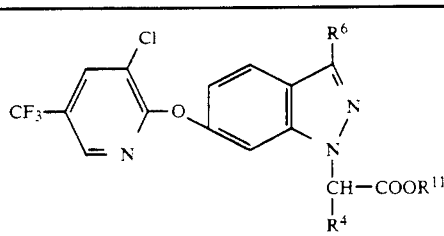

| Compound No. | $R^4$ | $R^{11}$ | $R^6$ |
|---|---|---|---|
| 37 | $CH_3$ | $C_2H_5$ | H |
| 38 | H | $C_2H_5$ | H |
| 39 | H | $C_2H_5$ | Cl |

TABLE IV

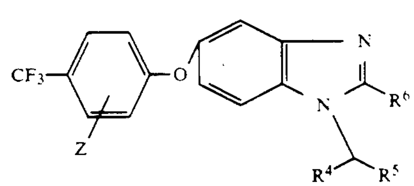

| COMPOUND | $R^4$ | $R^5$ | $R^6$ | Z |
|---|---|---|---|---|
| 61 | $CH_3$ | COOEt | $CF_3$ | 2-Cl, 6-F |
| 62 | $CH_3$ | COOEt | $CH_3$ | 2-Cl, 6-F |
| 63 | $CH_3$ | COOEt | $CH_3$ | 2-Cl |
| 64 | $CH_3$ | COOEt | H | $2\text{-}NO_2$ |
| 65 | $CH_3$ | COOEt | H | 2-CN |
| 66 | $CH_3$ | COOEt | H | 2-Cl |
| 67 | $CH_3$ | COOEt | H | 2-Cl, 6-F |
| 68 | H | COOEt | H | 2-Cl, 6-F |
| 69 | H | COOEt | $CF_3$ | 2-Cl, 6-F |
| 70 | H | COOEt | $CF_3$ | 2-CN |
| 71 | H | COOEt | $CF_3$ | 2-Cl |
| 72 | H | COOH | $CF_3$ | 2-Cl, 6-F |
| 73 | H | $CONH_2$ | $CF_3$ | 2-Cl, 6-F |
| 74 | H | CONHEt | $CF_3$ | 2-Cl, 6-F |
| 100 | $CH_3$ | COOEt | CN | 2-Cl, 6-F |
| 102 | $CH_3$ | COOMe | CN | 2-Cl, 6-F |
| 103 | $CH_3$ | COOiPr | CN | 2-Cl, 6-F |
| 104 | H | COOMe | CN | 2-Cl, 6-F |
| 108 | H | COOEt | $CF_3$ | $2\text{-}NO_2$ |

TABLE V

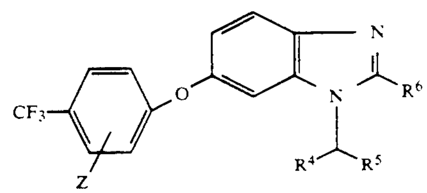

| COMPOUND | $R^4$ | $R^5$ | $R^6$ | Z |
|---|---|---|---|---|
| 75 | Me | COOEt | $CF_3$ | 2-Cl, 6-F |
| 76 | Me | COOH | $CF_3$ | 2-Cl, 6-F |
| 77 | Me | COOEt | Me | 2-Cl, 6-F |
| 78 | Me | COOEt | Me | 2-Cl |
| 79 | Me | COOEt | H | $2\text{-}NO_2$ |
| 80 | Me | COOEt | H | 2-CN |
| 81 | Me | COOEt | H | 2-Cl |
| 82 | Me | COOEt | H | 2-Cl, 6-Cl |
| 83 | H | COOEt | H | 2-Cl, 6-F |
| 84 | H | COOEt | $CF_3$ | 2-Cl, 6-F |
| 85 | H | COOEt | $CF_3$ | 2-CN |
| 86 | H | COOEt | $CF_3$ | 2-Cl |
| 87 | H | COOH | $CF_3$ | 2-Cl, 6-F |
| 88 | H | $CONH_2$ | $CF_3$ | 2-Cl, 6-F |
| 89 | H | CONHEt | $CF_3$ | 2-Cl, 6-F |
| 90 | H | $CONEt_2$ | $CF_3$ | 2-Cl, 6-F |
| 91 | H | CONH | $CF_3$ | 2-Cl, 6-F |
| 101 | $CH_3$ | COOEt | CN | 2-Cl, 6-F |
| 105 | $CH_3$ | COOMe | CN | 2-Cl, 6-F |
| 106 | $CH_3$ | COOiPr | CN | 2-Cl, 6-F |
| 107 | $CH_3$ | COOsecBu | CN | 2-Cl, 6-F |
| 109 | H | COOEt | $CF_3$ | 2-Cl, 6-Cl |

Compound 56

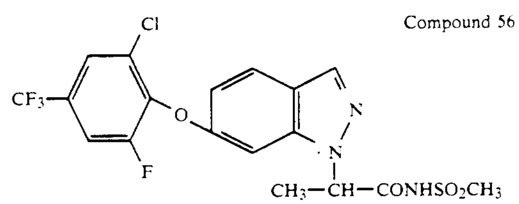

Compound 92

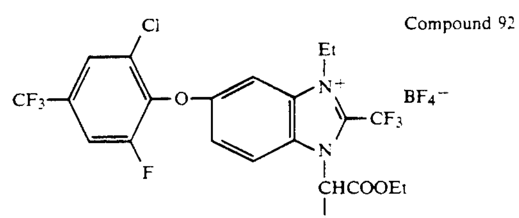

Compound 93

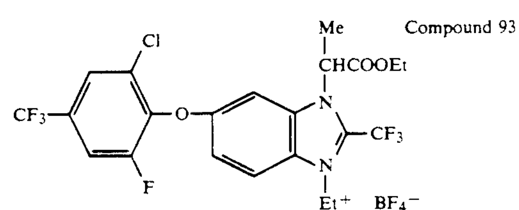

Compound 94

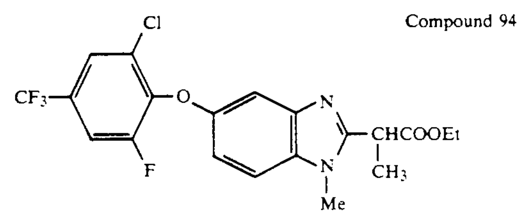

-continued

Compound 95

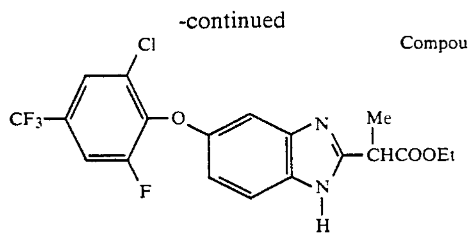

Compound 96

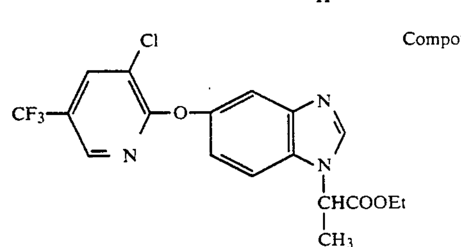

Compound 97

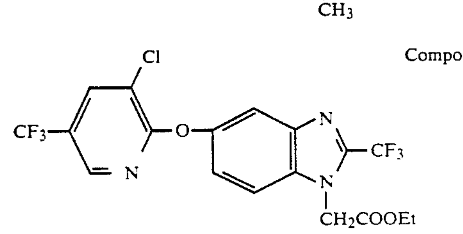

Compound 98

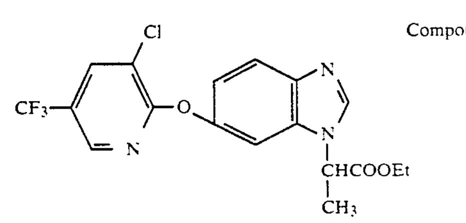

Compound 99

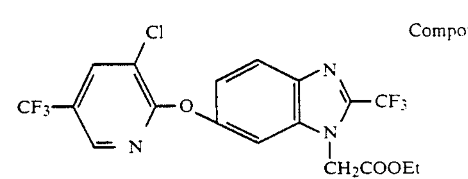

TABLE VI

| Compound No. | Characterising Data (NMR) |
|---|---|
| 1 | $CDCl_3$: δ 1.15(t)3H; 1.88(d)3H; 4.14(q)2H; 5.18(q)1H; 6.77(s)1H; 6.86(dd)1H; 7.41(dd)1H; 7.61(s)1H; 7.68(d)1H; 8.0(s)1H. |
| 2 | $CDCl_3$: δ 1.22(t)3H; 4.19(t)2H; 5.04(s)2H; 6.70(s)1H; 6.86(dd)1H; 7.43(dd)1H; 7.61(s)1H; 7.69(d)1H; 8.01(s)1H. |
| 3 | DMSO: δ 1.51(d)3H; 5.41(q)1H; 6.88(dd)1H; 7.14(s)1H; 7.73(d)1H; 8.02(m)3H. |
| 4 | DMSO: δ 5.11(s)2H; 6.91(dd)1H; 7.17(s)1H; 7.75(d)1H; 8.01(m)3H. |
| 5 | $CDCl_3$: δ 3.73(s)3H; 5.07(s)2H; 6.71(s)1H; 6.86(dd)1H; 7.44(dd)1H; 7.62(s)1H; 7.69(d)1H; 8.01(s)1H. |
| 6 | $CDCl_3$: δ 1.11(t)3H; 1.88(d)3H; 4.13(q)2H; 5.15(q)1H; 6.65(s)1H; 6.80(dd)1H; 7.66(d)1H; 7.70(s)2H; 7.99(s)1H. |
| 7 | $CDCl_3$: δ 1.17(t)3H; 1.91(d)3H; 4.17(q)2H; 5.24(q)1H; 6.94(dd)1H; 7.07(d)1H; 7.15(s)1H; 7.70(dd)1H; 7.79(d)1H; 8.09(s)1H; 8.25(s)1H. |
| 8 | $CDCl_3$: δ 1.18(t)3H; 1.91(d)3H; 4.16(q)2H; 5.26(q)1H; 6.92(m)2H; 7.17(s)1H; 7.68(dd)1H; 7.81(d)1H; |

TABLE VI-continued

| Compound No. | Characterising Data (NMR) |
|---|---|
| | 7.95(s)1H; 8.09(s)1H. |
| 9 | $CDCl_3$: δ 1.16(t)3H; 1.89(d)3H; 4.15(q)2H; 5.21(q)1H; 6.89(dd)1H; 6.96(d)1H; 6.99(s)1H; 7.43(dd)1H; 7.73(m)2H; 8.04(s)1H. |
| 10 | $CDCl_3$: δ 1.89(d)3H; 3.68(s)3H; 5.20(q)1H; 6.78(s)1H; 6.84(dd)1H; 7.43(dd)1H; 7.61(s)1H; 7.68(d)1H; 8.01(s)1H. |
| 11 | $CDCl_3$: δ 0.74(t)3H; 1.50(m)2H; 1.89(d)3H; 4.02(t)2H; 5.18(q)1H; 6.78(s)1H; 6.84(dd)1H; 7.41(dd)1h; 7.60(S)1h; 7.68(d)1H; 8.00(s)1H. |
| 12 | $CDCl_3$: δ 0.80(t)3H; 1.15(m)3H; 1.45(m)2H; 1.89(d)3H; 4.06(t)2H; 5.16(q)1H; 6.78(s)1H; 6.84(dd)1H; 7.41(dd)1H; 7.61(s)1H; 7.67(d)1H; 8.00(s)1H. |
| 13 | $CDCl_3$: δ 1.15(t)3H; 1.86(d)3H; 4.15(q)2H; 4.09(q)1H; 6.71(s)1H; 6.90(dd)1H; 7.43(dd)1H; 7.63(m)2H. |
| 14 | $CDCl_3$: δ 1.15(t)3H; 1.89(d)3H; 4.15(q)2H; 5.20(q)1H; 6.81(m)2H; 7.70(d)1H; 7.90(s)1H; 8.01(m)2H. |
| 15 | $CDCl_3$: δ 1.14(t)3H; 1.88(d)3H; 4.13(q)2H; 5.17(q)1H; 6.78(m)2H; 7.67(d)1H; 8.03(m)2H; 8.18(s)1H. |
| 16 | $CDCl_3$: δ 1.14(t)3H; 1.88(d)3H; 4.13(q)2H; 5.19(q)1H; 6.81(m)2H; 7.71(d)1H; 7.95(s)1H; 8.02(s)1H; 8.17(s)1H. |
| 17 | $CDCl_3$: δ 1.14(t)3H; 1.87(d)3H; 4.14(q)2H; 5.19(q)1H; 6.78(dd)1H; 6.85(s)1H; 7.69(d)1H; 8.02(s)1H; 7.44(s)1H. |
| 19 | $CDCl_3$: δ 1.86(d)3H; 5.01(q)1H; 5.39(bs)1H; 6.34(bs)1H; 6.72(s)1H; 6.95(dd)1H; 7.45(dd)1H; 7.63(s)1H; 7.72(d)1H; 8.09(s)1H. |
| 20 | D6 DMSO: δ 1.66(d)3H; 3.52(s)9H; 5.35(q)1H; 6.93(dd)1H; 7.14(s)1H; 7.80(d)1H; 8.10(m)3H. |
| 21 | $CDCl_3$: δ 1.21(t)3H; 4.20(q)2H; 5.08(s)2H; 6.92(m)2H; 6.99(d)1H; 7.44(dd)1H; 7.75(m)2H; 8.06(s)1H. |
| 22 | $CDCl_3$: δ 1.26(t)3H; 4.22(q)2H; 5.10(s)2H; 6.95(dd)1H; 7.06(m)2H; 7.70(dd)1H; 7.80(d)1H; 8.08(s)1H; 8.25(s)1H. |
| 23 | $CDCl_3$: δ 1.26(t)3H; 4.22(q)2H; 5.12(s)2H; 6.95(m)3H; 7.12(s)1H; 7.69(dd)1H; 7.82(d)1H; 7.94(s)1H; 8.09(s)1H. |
| 24 | $CDCl_3$: δ 1.24(t)3H; 4.20(q)2H; 4.99(s)2H; 6.85(s)1H; 6.95(dd)1H; 7.03(d)1H; 7.48(dd)1H; 7.69(d)1H; 7.78(s)1H. |
| 25 | $CDCl_3$: δ 1.27(t)3H; 4.12(q)2H; 5.04(s)2H; 7.00(dd)1H; 7.04(s)1H; 7.10(d)1H; 7.74(d)2H; 8.28(s)1H. |
| 26 | $CDCl_3$: δ 1.27(t)3H; 4.13(q)2H; 5.04(s)2H; 6.93(d)1H; 7.02(dd)1H; 7.09(s)1H; 7.70(dd)1H; 7.76(d)1H; 7.95(s)1H. |
| 27 | D6DMSO: δ 5.12(s)2H; 7.00(dd)1H; 7.22(s)1H; 7.62(d)1H; 7.98(m)2H. |
| 28 | $CDCl_3$: δ 3.74(s)3H; 4.99(s)2H; 6.66(d)1H; 6.91(dd)1H; 7.44(dd)1H; 7.64(s+d)2H. |
| 29 | $CDCl_3$: δ 0.82(t)3H; 1.58(m)2H; 4.09(t)2H; 4.97(s)2H; 6.65(s)1H; 6.91(dd)1H; 7.43(dd)1H; 7.63(s+d)2H. |
| 30 | $CDCl_3$: δ 0.86(t)3H; 1.25(m)3H; 1.54(m)3H; 4.12(q)2H; 4.98(s)2H; 6.66(s)1H; 6.91(dd)1H; 7.44(dd)1H; 7.64(s+d)2H. |
| 31 | $CDCl_3$: δ 1.22(t)3H; 4.19(q)2H; 4.96(s)2H; 6.66(s)1H; 6.91(dd)1H; 7.43(dd)1H; 7.62(s+d)2H. |
| 32 | $CDCl_3$: δ 1.75(d)6H; 1.80(d)2.4H; 2.48(s)6H; 5.01(q)0.8H; 5.71(q)02H; |

TABLE VI-continued

| Compound No. | Characterising Data (NMR) |
|---|---|
| | 6.11(s)0.2H; 6.69(s)0.8H; 6.87(dd)0.2H; 6.97(dd)0.8H; 7.46(dd)1H; 7.62(s)1H; 7.66(d)0.2H; 7.73(d)0.8H; 8.0(s)0.2H; 8.09(s)0.8H. |
| 33 | $CDCl_3$: δ 1.24(t)3H; 1.89(d)3H; 4.19(q)2H; 5.27(q)1H; 6.78(s)1H; 7.01(dd)1H; 7.39(dd)1H; 7.59(s)1H; 7.68(d)1H; 8.04(s)1H. |
| 34 | $CDCl_3$: δ 1.28(t)3H; 4.25(q)2H; 5.11(s)2H; 6.78(s)1H; 7.0(dd)1H; 7.40(dd)1H; 7.59(s)1H; 7.67(d)1H; 7.99(s)1H. |
| 35 | $CDCl_3$: δ 1.90(d)3H; 3.73(s)3H; 5.29(q)1H; 7.01(dd)1H; 7.40(dd)1H; 7.59(s)1H; 7.66(d)1H; 8.03(s)1H. |
| 36 | d6 DMSO: δ 1.69(d)3H; 5.28(q)1H; 6.77(s)1H; 6.91(dd)1H; 7.75(d)1H; 7.99(s+d)2H; 8.41(s)1H. |
| 37 | $CDCl_3$: δ 1.16(t)3H; 1.80(d)3H; 4.16(q)2H; 5.26(q)1H; 6.98(dd)1H; 7.24(s)1H; 7.78(d)1H; 8.0(s)1H; 8.06(s)1H; 8.26(s)1H. |
| 38 | $CDCl_3$: δ 1.25(t)3H; 4.21(q)2H; 5.12(s)2H; 7.00(dd)1H; 7.18(s)1H; 7.80(d)1H; 8.02(s)1H; 8.09(s)1H; 8.27(s)1H. |
| 39 | $CDCl_3$: δ 1.24(t)3H; 4.21(q)2H; 5.04(s)2H; 7.05(dd)1H; 7.15(s)1H; 7.74(d)1H; 8.0(s)1H; 8.25(s)1H. |
| 40 | d6DMSO: δ 1.64(d)3H; 5.61(q)1H; 7.05(dd)1H; 7.28(d)1H; 7.66(d)1H; 8.04(m)2H. |
| 41 | $D_2O$: δ 1.52(d)1H; 4.80(q)1H; 6.60(dd)1H; 6.68(s)1H; 7.33(d)1H; 7.45(d)1H; 7.48(s)1H; 7.84(s)1H. |
| 42 | $CDCl_3$: δ 1.86(d)3H; 3.68(s)3H; 5.11(q)1H; 6.72(s)1H; 6.89(dd)1H; 7.43(dd)1H; 7.62(m)2H. |
| 43 | $CDCl_3$: δ 1.10(dd)6H; 4.98(m)1H; 5.06(q)1H; 6.70(d)1H; 6.91(dd)1H; 7.42(dd)1H; 7.62(m)2H. |
| 44 | $CDCl_3$: δ 0.80(t)3H; 1.15(m)2H; 1.46(m)2H; 1.87(d)3H; 4.06(t)2H; 5.09(q)1H; 6.72(d)1H; 6.89(dd)1H; 7.44(dd)1H; 7.62(m)2H. |
| 45 | $CDCl_3$: δ 0.74(t)3H; 1.50(m)2H; 1.88(d)3H; 4.03(t)2H; 5.10(q)1H; 6.71(d)1H; 6.90(dd)1H; 7.43(dd)1H; 7.62(m)2H. |
| 46 | $CDCl_3$: δ 1.88(d)3H; 3.25(s)3H; 3.48(m)2H; 4.24(m)2H; 5.15(q)1H; 6.75(s)1H; 6.89(dd)1H; 7.44(d)1H; 7.61(m)2H. |
| 47 | $CDCl_3$: δ 1.56(s)3H; 1.96(s+d)6H; 5.23(q)1H; 6.76(d)1H; 6.92(dd)1H; 7.44(dd)1H; 7.63(m)2H. |
| 48 | $CDCl_3$: δ 1.14(t)3H; 1.86(d)3H; 4.13(q)2H; 5.08(q)1H; 6.60(d)1H; 6.85(dd)1H; 7.63(d)1H; 7.72(s)2H. |
| 49 | $CDCl_3$: δ 1.20(t)3H; 1.91(d)3H; 1.16(q)2H; 5.18(q)1H; 6.94(d)1H; 6.99(dd)1H; 7.15(s)1H; 7.71(dd)1H; 7.76(d)1H; 7.96(s)1H. |
| 50 | $CDCl_3$: δ 1.14(t)3H; 1.86(d)3H; 4.14(q)2H; 5.10(q)1H; 6.76(d)1H; 6.85(dd)1H; 7.65(d)1H; 7.91(s)1H; 8.00(d)1H. |
| 51 | $CDCl_3$: δ 2.01(d)3H; 5.45(q)1H; 6.88(m)2H; 7.43(dd)1H; 7.62(s)1H; 7.69(q)4H; 7.72(d)1H; 8.06(s)1H. |
| 52 | $CDCl_3$: δ 1.50(s)3H; 1.92(s)3H; 1.98(d)3H; 5.30(q)1H; 6.80(s)1H; 6.86(dd)1H; 7.42(dd)1H; 7.61(s)1H; 7.68(d)1H; 8.01(s)1H. |
| 53 | $CDCl_3$: δ 1.86(d)3H; 5.11(q)1H; 6.62(d)1H; 6.86(dd)1H; 7.62(d)1H; 7.72(s)2H. |
| 54 | $CDCl_3$: δ 1.92(d)3H; 5.22(q)1H; 6.94(d)1H; 6.99(dd)1H; 7.13(s)1H; 7.72(dd)1H; 7.75(d)1H; 7.96(d)1H. |
| 55 | $CDCl_3$: δ 1.89(d)3H; 5.14(q)1H; |

TABLE VI-continued

| Compound No. | Characterising Data (NMR) |
|---|---|
| | 6.76(s)1H; 6.86(dd)1H; 6.65(d)1H; 7.90(s)1H; 8.00(s)1H. |
| 56 | D6DMSO: δ 1.54(d)3H; 3.14(s)3H; 5.39(q)1H; 6.86(dd)1H; 7.08(s)1H; 7.73(d)1H; 7.98(m)2H; 8.05(s)1H. |
| 61 | $CDCl_3$: δ 1.18(t)3H; 1.82(d)3H; 4.20(q)2H; 5.35(q)1H; 7.19(m)2H; 7.39(m)2H; 7.60(s)1H. |
| 62 | $CDCl_3$: δ 1.15(t)3H; 1.75(d)3H; 2.6(s)3H; 4.15(q)2H; 5.05(q)1H; 6.8(dd)1H; 6.9(d)1H; 7.4(dd)1H; 7.6(d+s)2H. |
| 63 | $CDCl_3$: δ 1.2(t)3H; 1.85(d)3H; 2.65(s)3H; 4.2(q)2H; 5.1(q)1H; 6.85(d)1H; 6.95(dd)1H; 7.3(d)1H; 7.4(dd+d)2H; 7.7(s)1H. |
| 64 | $CDCl_3$: δ (1.25(t)3H; 1.95(d)3H; 4.25(q)2H; 5.15(q)1H; 7.0(d)1H; 7.1(dd)1H; 7.45(d)1H; 7.55(d)1H; 7.65(dd)1H; 8.15(s)1H; 8.25(d)1H. |
| 65 | $CDCl_3$: δ (1.4(t)3H; 2.05(d)1H; 4.35(q)2H; 5.3(?)1H; 7.0(d)1H; 7.2(dd)1H; 7.6(d)1H; 7.7(d)1H 7.8(dd)1H; 8.05(d)1H; 8.3(s)1H. |
| 66 | $CDCl_3$: δ 1.25(t)3H; 1.9(d)3H; 4.2(q)2H; 5.15(q)1H; 6.9(d)1H; 7.05(dd)1H; 7.4(dd+d)2H; 7.5(d)1H; 7.75(d)1H; 8.15(s)1H. |
| 67 | $CDCl_3$: δ 1.25(t)3H; 1.9(d)2H; 4.2(q)2H; 5.1(q)1H; 7.05(dd+d)2H; 7.3(d)1H; 7.7(s)2H; 8.05(s)1H. |
| 68 | $CDCl_3$: δ 1.3(t)3H; 4.25(q)2H; 5.1(s)2H; 7.1(dd)1H; 7.2(d)1H; 7.25(d)1H; 7.4(dd)1H; 7.6(s)1H; 7.9(s)1H. |
| 69 | $CDCl_3$: δ 1.25(t)3H; 4.25(q)2H; 5.0(s)2H; 7.25(m)2H; 7.325(d)1H; 7.4(dd)1H; 7.0(s)1H. |
| 70 | $CDCl_3$: δ 1.3(t)3H; 4.3(q)2H; 5.05(s)2H; 6.9(d)1H; 7.275(dd)1H; 7.45(d)1H; 7.7(m)2H; 7.95(d)1H. |
| 71 | $CDCl_3$: δ 1.3(t)3H; 4.275(q)2H; 5.05(s)2H; 6.925(d)1H; 7.225(dd)1H; 7.4(m)2H; 7.525(d)1H; 7.75(d)1H. |
| 72 | $CDCl_3$ δ 3.4–4.2(broad hump)1H; 5.0(s)2H; 5.0(s)2H; 7.225(m)2H; 7.4(m)2H; 7.6(s)1H. |
| 73 | m.p. 250.2–252.2° C. $m^+ = 454$ |
| 74 | $CDCl_3$: δ 1.1(t)3H; 3.3(quintet)2H; 4.9(s)2H; 5.45(t)1H; 7.25(m)2H; 7.4(m)2H; 7.6(s)1H. |
| 75 | $CDCl_3$: δ 1.13(t)3H; 1.80(d)3H; 4.18(q)2H; 5.30(q)1H; 6.95(m)2H; 7.40(dd)1H; 7.60(s)1H; 7.81(d)1H. |
| 76 | DMSO: δ 1.60(d)3H; 5.38(q)1H; 7.04(dd)1H; 7.24(d)1H; 7.80(d)1H; 8.01(m)2H. |
| 77 | $CDCl_3$: δ 1.2(t)3H; 1.8(d)3H; 2.6(s)3H; 4.2(q)2H; 5.01(q)1H; 7.25(d)1H; 7.04(dd)1H; 7.6(s)1H. |
| 78 | $CDCl_3$: δ 1.2(t)3H; 1.8(d)3H; 2.65(t)3H; 4.2(q)2H; 5.1(q)1H; 6.85(d)1H; 6.95(dd)1H; 7.1(d)1H; 7.4(dd)1H; 7.7(d+s)2H. |
| 79 | $CDCl_3$: δ 1.25(t)3H; 1.9(d)3H; 4.2(q)2H; 5.1(q)1H; 7.05(dd+d)2H; 7.2(d)1H; 7.7(dd)1H; 7.85(dd)1H; 8.15(s)1H; 8.25(d)1H. |
| 80 | $CDCl_3$: δ 1.25(t)3H; 1.9(d)3H; 4.2(q)2H; 5.1(q)1H; 6.9(d)1H; 7.05(dd)1H; 7.2(d)1H; 7.7(dd)1H; 7.85(d)1H; 7.95(d)1H; 8.15(s)1H. |
| 81 | $CDCl_3$: δ 1.25(t)3H; 1.9(d)3H; 4.2(q)2H; 5.05(q)1H; 6.9(d)1H; 7.0(dd)1H; 7.1(d)1H; 7.4(dd)1H; 7.75(d)1H; 7.85(d)1H; 8.1(s)1H. |
| 82 | $CDCl_3$: δ 1.2(t)3H; 1.85(d)3H; 4.2(q)2H; 5.0(q)1H; 6.8(dd+d)2H; 7.7(m)1H; 8.05(s)1H. |
| 83 | $CDCl_3$: δ 1.25(t)3H; 4.25(q)2H; |

TABLE VI-continued

| Compound No. | Characterising Data (NMR) |
|---|---|
| | 4.8(s)1H; 6.85(d)1H; 6.9(dd)1H; 7.4(dd)1H; 7.6(s)1H; 7.75(d)1H; 7.9(s)1H. |
| 84 | $CDCl_3$: δ 1.25(t)3H; 4.25(q)2H; 4.95(s)2H; 6.85(d)1H; 7.0(dd)1H; 7.425(dd)1H; 7.6(s)1H; 7.85(d)1H. |
| 85 | $CDCl_3$: δ 1.25(t)3H; 4.25(q)2H; 5.0(s)2H; 6.9(d)1H; 7.15(m)2H; 7.7(dd)1H; 7.95(m)2H. |
| 86 | $CDCl_3$: δ 1.25(t)3H; 4.25(q)2H; 4.975(s)2H; 6.95(d)1H; 7.025(d)1H; 7.125(dd)1H; 7.45(dd)1H; 7.75(d)1H; 7.9(d)1H. |
| 87 | $CDCl_3$: δ 4.8-5.2(broad)1H; 4.9(s)2H; 6.875(d)1H; 7.0(dd)1H; 7.425(dd)1H; 7.6(s)1H; 7.825(d)1H. |
| 88 | Mass Spec. $M^+$ =455 $MH^+$ =456 m.p. 236.7-237.7° C. |
| 89 | $CDCl_3$: δ 1.05(t)3H; 3.25(q)2H; 4.85(s)2H; 5.45(t)1H; 6.875(d)1H; 7.1(dd)1H; 7.42(dd)1H; 7.6(s)1H; 7.85(d)1H. |
| 90 | $CDCl_3$: δ 1.1(t)3H; 1.25(t)3H; 3.4(q)4H; 5.0(s)2H; 6.85(d)1H; 6.92(dd)1H; 7.4(dd)1H; 7.55(s)1H; 7.8(d)1H. |
| 91 | $CDCl_3$: δ (5.025(s)2H; 6.95(m)2H; 7.1(t)1H; 7.3(m)3H; 7.47(d)2H; 7.55(s)1H; 7.8(d)1H; 9.35(s)1H. |
| 92 | m.p. 166.1-167.5° C. |
| 93 | m.p. 135-136.1° C. |
| 94 | m.p. 123.2-128.6° C. |
| 95 | $CDCl_3$: δ 1.1(t)3H; 1.5(d)3H; 3.95-4.2(m)3H; 6.9(dd)1H; 7.0(d)1H; 7.5(d)1H; 7.95(d+s)2H. |
| 96 | $CDCl_3$: δ 1.25(t)3H; 1.9(d)3H; 4.2(q)2H; 5.15(q)1H; 7.15(dd)1H; 7.45(d)1H; 7.65(d)1H; 8.00(d)1H; 8.15(s)1H; 8.25(d)1H. |
| 97 | $CDCl_3$: δ 1.25(t)3H; 4.25(q)2H; 5.05(s)2H; 7.3(dd)1H; 7.425(d)1H; 7.725(d)1H; 8.0(d)1H; 8.25(s)1H. |
| 98 | $CDCl_3$: δ 1.25(t)3H; 1.9(d)3H; 4.2(q)2H; 5.1(q)1H; 7.1(dd)1H; 7.25(d)1H; 7.85(d)1H; 8.0(d)1H; 8.15(s)1H; 8.25(s)1H. |
| 99 | $CDCl_3$: δ 1.25(t)3H; 4.2(q)2H; 5.0(s 2H; 7.2(m)2H; 7.95(d)1H; 8.0(d)1H; 8.25(s)1H. |
| 100 | $CDCl_3$: δ 1.25(t)3H; 1.95(d)3H; 4.25(q)2H; 5.4(q)1H; 7.15(d)1H; 7.27(dd)1H; 7.44(ddx 2)2H; 7.62(s)1H. |
| 101 | $CDCl_3$: δ 1.25(t)3H; 1.9(d)3H; 4.25(q)2H; 5.35(q)1H; 6.92(d)1H; 7.02(dd)1H; 7.62(s)1H; 7.45(dd)1H; 7.8(d)1H. |
| 102 | $CDCl_3$: δ 1.95(d)3H; 3.8(S)3h; 5.45(Q)1h; 7.15(D)1h; 7.2(DD)1h; 7.45(D)2h; 7.63(S)1h. |
| 103 | $CDCl_3$: δ 1.17(d)3H; 1.28(d)3H; 1.95(d)3H; 5.1(q)1H; 5.35(q)1H; 7.15(d)1H; 7.25(dd)1H; 7.42(d)2H; 7.63(s)1H. |
| 104 | $CDCl_3$: δ 3.85(s)3H; 5.1(s)2H; 7.18(s)1H; 7.3(d)2H; 7.45(dd)1H; 7.63(s)1H. |
| 105 | $CDCl_3$: δ 1.93(d)3H; 3.8(s)3H; 5.35(q)1H; 6.93(d)1H; 7.02(dd)1H; 7.45(dd)1H; 7.63(s)1H; 7.8(d)1H. |
| 106 | $CDCl_3$: δ 1.15(d)3H; 1.25(d)3H; 1.9(d)3H; 5.06(q)1H; 5.3(q)1H; 6.9(d)1H; 7.03(dd)1H; 7.45(d)1H; 7.63(s)1H; 7.8(d)1H. |
| 107 | $CDCl_3$: δ (0.85+0.652xt) 3H; 1.1-1.2(2xd)3H; 1.4-1.6(m)2H; 1.9(q)3H; 4.9(m)1H; 5.3(q)1H; 6.9(m)1H; 7.02(m)1H; 7.45(dd)1H; 7.65(s)1H; 7.8(d)1H. |
| 108 | $CDCl_3$: δ 1.3(t)3H; 4.3(q)2H; 5.08(s)2H; 7.02(d)1H; 7.25(dd)1H; 7.45(d)1H; 7.65(d)1H; 7.77(dd)1H; 8.35(d)1H. |
| 109 | $CDCl_3$: δ 1.25(t)3H; 4.2(q)2H; 4.9(s)2H; 6.8(d)1H; 6.95(dd)1H; 7.7(s)2H; 7.82(d)1H. |

Compounds of formula (I) may be prepared by the following general processes:

a) reacting a compound of formula (II'):

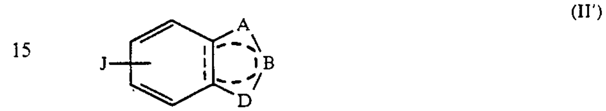

where A, B and D are as defined in relation to formula (I) and J is OH or $CF_3CONH$ with a compound of formula (III):

Ar—Z (III)

where Ar is as defined in relation to formula (I) and Z is a leaving group, optionally in the presence of a base; or b) reacting a compound of formula (XXXXI):

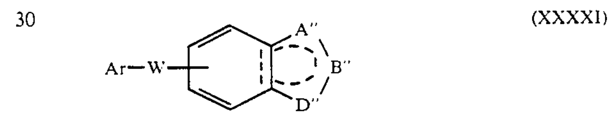

where Ar and W are as defined in relation to formula (I) and A'', B'' and D'' are independently selected from N, $NR^2$, NH, $CR^6$, CH or $CHR^6$; provided 2 of A'', B'' and D'' are N, $NR^2$ or NH and at least one of A, B or D carries a hydrogen atom with a compound of formula (VII):

$$R^3-\underset{XR^5}{\overset{Z}{C}}-R^4 \quad (VII)$$

where X, $R^3$, $R^4$ and $R^5$ are as defined in relation to formula (I) and Z is a leaving group in an organic solvent in the presence of a base; or c) cyclisation of compounds of formula (XXXXII):

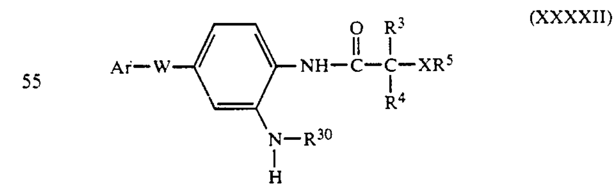

wherein Ar, W, X, $R^3$, $R^4$ and $R^5$ are as defined in relation to formula (I) and $R^{30}$ is H or lower alkyl in the presence of a dehydrating agent. Further details for these general processes are set out below.

Compounds of formula (IA) may be prepared by reacting a compound of formula (II):

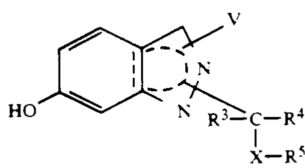

wherein V, X, $R^3$, $R^4$ and $R^5$ are as defined in relation to formula (IA) with a compound of formula (III):

$$Ar—Z \quad (III)$$

wherein Ar is as defined in relation to formula (I) and Z is a leaving group, optionally in the presence of a base.

Suitable leaving groups Z include halide, such as fluoride, bromide and chloride, and sulphonates such as methanesulphonate and p-toluenesulphonate.

Suitable bases for use in the reaction include bases such as sodium hydride, and alkali metal carbonates and hydroxides.

The reaction is preferably carried out in an organic solvent such as dimethylformamide, dimethylsulphoxide, a lower alkanol, or a lower ketone. Moderate temperatures, for example of from 20° to 120° C. are suitably employed. Conveniently the reaction is carried out at 100° to 110° C.

Compounds of formula (II) can be prepared from compounds of formula (IV):

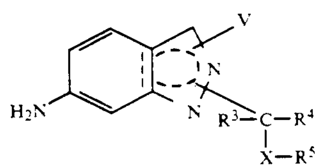

wherein V, X, $R^3$, $R^4$ and $R^5$ are as defined in relation to formula (IA), by diazotisation with nitrous acid followed by aqueous acidic hydrolysis e.g. according to the procedure described in J. Org. Chem (1977), 42(12), 2053.

Alternatively compounds of formula (II) where V is other than cyano can be prepared from compounds of formula (IV) by reaction with water and sulphuric acid at 150°-170° C. and 100-120 psi; e.g. according to the procedure described in J. C. S. (1955) 2412.

Compounds of formula (II) are novel and as such form a further aspect of the invention.

Compounds of formula (IV) are prepared by reduction of the corresponding nitro compound of formula (V) where V, X, $R^3$, $R^4$ and $R^5$ are as defined in relation to formula (IA).

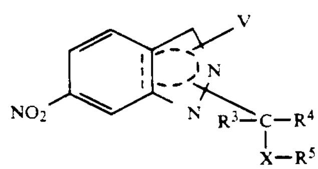

A wide variety of reducing agents may be used and may be selected form the chemical literature by the skilled worker in the art. The reduction may be carried out for example by using sodium dithionite or tin and hydrochloric acid, iron and hydrochloric acid, reduced iron with hydrochloric acid in isopropanol or hydrogen with a palladium on charcoal catalyst. The reaction is preferably effected in an organic solvent such as a lower alkyl alcohol optionally mixed with water at temperatures of from 20° C. to 90° C.

Compounds of formula (IV) are novel and as such form a further aspect of the invention.

Compounds of formula (V) can be prepared from compounds of formula (VI):

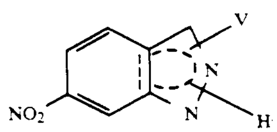

by reaction with compounds of formula (VII):

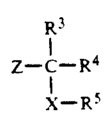

wherein X, $R^3$, $R^4$ and $R^5$ are as defined in relation to formula (IA) and Z is a leaving group as hereinbefore defined in solvents such as dimethylformamide, dimethylsulphoxide or lower alkyl ketones in the presence of a base such as sodium hydride, alkali metal carbonates or hydroxides at temperatures from 20° to 80° C.

Compounds of formula (V) are novel and as such form a further aspect of the invention.

Compounds of formula (III), (VI) and (VII) are known compounds or they can be prepared from known compounds by known methods.

Compounds of formula (IA) where the Ar-W is attached at positions other than the 6 position of the indazole ring may be made starting from the appropriate nitro analogue of compounds of formula (VI). These analogues may be prepared using methods known in the art.

Compounds of formula (IA) where W is NH may be prepared by reacting a compound of formula (VIII):

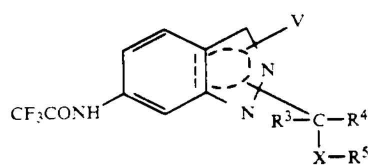

wherein X, $R^3$, $R^4$ and $R^5$ are as defined in relation to formula (I) with sodium hydride in dimethylformamide or dimethylsulphoxide and reacting the anion so formed with a compound of formula (III) as herebefore defined in dimethylformamide or dimethylsulphoxide at temperatures of from 50° to 90° C.

Compounds of formula (VIII) may be prepared from compounds of formula (IV) as hereinbefore defined by reaction with trifluoroacetic anhydride according to the procedure described in J. Org. Chem., 1965, 30, 1287.

Compounds of formula (VIII) are novel and as such form a further aspect of the invention.

Compounds of formula (IA) produced by the foregoing method may be alkylated by standard techniques to produce compounds of formula (IA) where W is $NR^1$.

Compounds of formula (IA) where V is H attached to the carbon atom at the 3 position of the indazole and W is oxygen attached to the indazole ring at the 6 position may be prepared from compounds of formula (IX):

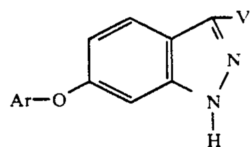

where Ar is as defined in relation to formula (IA) by reaction with a compound of formula (VII) as hereinbefore defined in solvents such as dimethylformamide, dimethylsulphoxide, lower alkanols, or lower alkanones at temperatures of from 60°-100° C. in the presence of a base such as sodium hydride, alkali metal carbonates or hydroxides.

Compounds of formula (IX) are prepared by deacylation of compounds of formula (X):

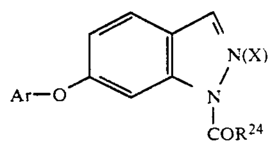

where $R^{24}$ is lower alkyl and Ar is as defined in relation to formula (IA).

Compounds of formula (IX) are novel and as such form a further aspect of the invention.

Compounds of formula (X) are prepared from compounds of formula (XI):

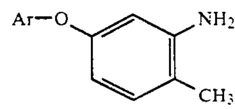

by a Jacobsen reaction (C. Ruchardt and V. Hassmann, Synthesis, 375, 1972 and F. Trondlin, R. Werner and C. Ruchardt Ber., 367, 111, 1978) using solvents such as benzene or toluene at temperatures of from 80°-110° C.

Compounds of formula (X) are novel and as such form a further aspect of the invention.

Compounds of formula (XI) are prepared by reduction of compounds of formula (XII).

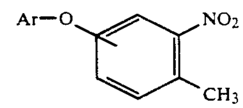

A wide variety of reducing agents may be used and may be selected form the chemical literature by the skilled worker in the art. The reduction may be carried out for example by using sodium dithionite or tin and hydrochloric acid, iron and hydrochloric acid, reduced iron with hydrochloric acid in isopropanol, or hydrogen with a palladium on charcoal catalyst. The reaction is preferably effected in an organic solvent such as a lower alkyl alcohol optionally mixed with water at temperatures of from 20° C. to 90° C.

Compounds of formula (XI) other than 4-(2,4-dichlorophenoxy)-2-methylaniline are novel and as such form a further aspect of the invention.

Compounds of formula (XII) are prepared by reacting a compound of formula (III) as hereinbefore defined with the known compound 4-methyl-3-nitrophenol in solvents such as dimethylformamide, dimethylsulphoxide or lower alkanones at temperatures of 90°-120° C. in the presence of a base such as sodium hydride, alkaline metal carbonates and hydroxides.

Compounds of formula (XII) other than 4-(2,4-dichlorophenoxy)-2-methylnitrobenzene are novel and as such form a further aspect of the invention.

The corresponding 5-aryloxy indazoles may be produced by an analogous process using appropriate starting materials.

Compounds of formula (IB):

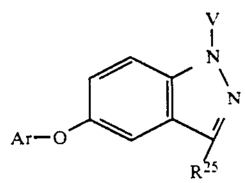

where Ar, and V, are as defined in relation to formula (IA) except V is not haloalkyl and $R^{25}$ is $CH_2COOR^{11}$ or $CH(CH_3)COOR^{11}$ where $R^{11}$ is as defined in relation to formula (IA) may be prepared from a compound of formula (IIB)

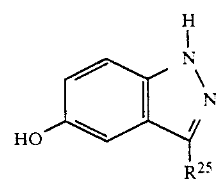

by reaction with compound of formula (III as described above in the reaction of compounds of formula (II) with formula (III).

The compound of formula (IIB) is prepared for example by the method of Fucher and Tafel Ann. 303, 227, 1885 as shown in the following scheme:

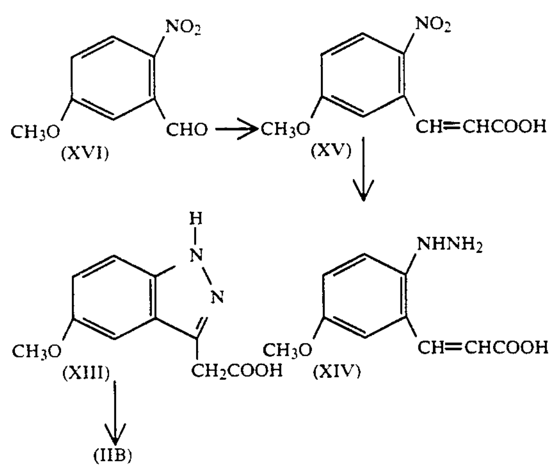

The compound of formula (IIB), may be prepared by demethylation of a compound of formula (XIII) using for example boron tribromide at −70° to −50° C. in dichloromethane optionally followed by esterification with the appropriate $R^{11}$ alcohol.

The compound of formula (XIII) may be formed by cyclisation of a compound of formula (XIV) by reaction with air at 0°-20° C. in aqueous sodium or potassium hydroxide solution.

The compound of formula (XIV) may be prepared by reduction of a compound of formula (XV) to its corresponding amine, diazotisation using sodium nitrite and concentrated hydrochloric acid followed by a further reduction of the diazonium compound with for example stannous chloride in hydrochloric acid or sodium sulphite and sulphur dioxide.

The compound of formula (XV) may be prepared from a compound of formula (XVI) by reaction with sodium acetate and acetic anhydride at 150°-180° C.

The compound of formula (XVI) is a known compound.

The scheme as shown produces compounds of formula (IB) where V is H. Further compounds of formula (IB) where V is other than H may be produced by standard methods. For example treatment of a compound of formula (IB) where V is H with a lower alkyl halide such as methyl iodide, or a lower alkyl sulphate such as dimethyl sulphate or diethyl sulphate would yield compounds where V is lower alkyl.

Alternatively treatment with a lower alkyl haloformate such as ethyl chloroformate would yield compounds of formula (IB) where V is COO-lower alkyl.

The scheme as shown also produces compounds of formula (IB) where $R^{25}$ is $CH_2COOR^{11}$. The treatment of these compounds with a base e.g. potassium t-butoxide, potassium or lithium bis(trimethylsilyl)amide at temperatures from 0° to −40° C. in THF with methyl iodide would yield the corresponding compounds of formula (IB) where $R^{25}$ is $CH(CH_3)COOR^{11}$.

The corresponding 6-aryloxyindazoles may be produced by an analogous process using appropriate starting materials.

An alternative method of preparing compounds of formula (XIII) is the method of Kariyone and Yagi C. A. 186340j, 93, 1980 as shown in the following scheme:

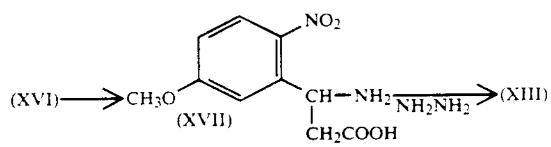

The compound of formula (XIII) may be prepared from a compound of formula (XVII) by reaction with activated charcoal and hydrazine hydrate in aqueous sodium hydroxide at 30° to 80° C.

The compound of formula (XVII) may be prepared from a compound of formula (XVI) as hereinbefore defined by reaction with malonic acid and ammonium formate in formic acid at 40° to 95° C.

Compounds of formula (IC) where W is oxygen, A is N, B is $CR^6$ and D is $NCR^3R^4XR^5$ may be prepared by reacting a compound of formula (XVIII):

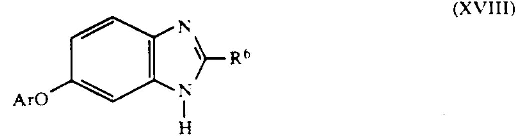

wherein Ar and $R^6$ are as defined in relation to formula (IC) with a compound of formula (VII) as hereinbefore defined in a suitable solvent e.g. dimethylsulphoxide, dimethylformamide, acetonitrile, a lower alkyl ketone in the presence of an appropriate base e.g. sodium hydride, alkyl metal carbonate at 50°-100° C.

This reaction produces two regio-isomers which may be readily separated by known techniques (e.g. chromatography or preparative tlc) to produce two compounds of formula (IC).

Compounds of formula (XVIII) can be prepared by cyclisation of compounds of formula (XIX):

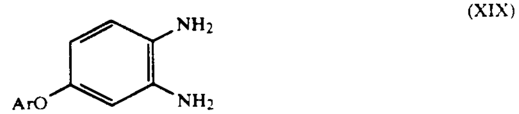

wherein Ar is as defined in relation to formula (IC), using an appropriate organic, aliphatic acid at 100°-120° C. with or without aqueous mineral acid e.g. hydrochloric acid.

Compounds of formula (XVIII) are novel and as such form a further aspect of the invention.

Compounds of formula (XIX) are prepared by reduction of the corresponding dinitro compound of formula (XX):

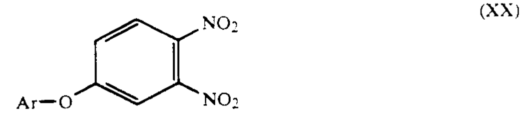

A wide variety of reducing agents may be used and may be selected from the chemical literature by the skilled worker in the art. The reduction may be carried out for example by using sodium borohydride with a palladium on charcoal catalyst. The reaction is preferably effected in an organic solvent such as a lower alcohol optionally mixed with water at temperatures of from −20° C. to 10° C.

Compounds of formula (XX) can be prepared by nitration of a compound of formula (XXI):

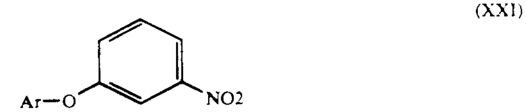

using a nitrating agent such as potassium nitrate mixed with concentrated sulphuric acid. The reaction is preferably carried out in a suitable solvent such as acetic anhydride, methylene dichloride, ethylene dichloride or concentrated sulphuric acid. Temperatures of from −20° C. to 25° C. are suitably employed.

Compounds of formula (XXI) are prepared by reacting m-nitrophenol with a compound of formula (III) as hereinbefore defined in an organic solvent, for example dimethylsulphoxide, lower alkyl ketones such as acetone or butanone, or lower glymes e.g. $MeOCH_2CH_2OMe$ in the presence of a base e.g. alkaline metal hydroxides (KOH) or carbonates ($K_2CO_3$) at a temperature of 50° to 120° C.

If it is desired to produce a compound of formula (IC) where the ArW is attached at other positions on the carbocyclic portion of the benzimidazole ring, the appropriate dinitro analogue of a compound of formula (XX) would be employed. These may be produced from known starting materials by methods known in the art.

Compounds of formula (XVIII) may alternatively be prepared from compounds of formula (XXII):

(XXII)

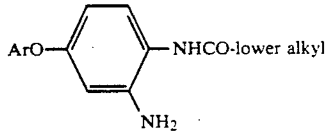

where Ar is as defined in relation to formula (IC) by heating in the appropriate lower aliphatic acid at 100°-120° C.

Compounds of formula (XXII) may be prepared by reduction of compounds of formula (XXIII):

(XXIII)

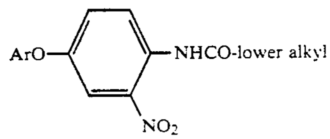

where Ar is as defined in relation to formula (IC) using a wide variety of reducing agents which may be selected from the chemical literature by those skilled in the art. The reduction may be carried out for example by using titanium trichloride in aqueous hydrochloric acid at 0° to 10° C.

Compounds of formula (XXIII) may be prepared by nitration of compounds of formula (XXIV):

(XXIV)

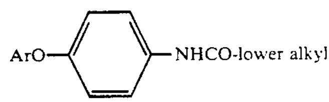

where Ar is as defined in relation to formula (IC) using a nitrating agent such as concentrated nitric acid in acetic anhydride at −10° C. to 0° C.

Compounds of formula (XXIV) may be prepared by reacting compounds of formula (XXV):

(XXV)

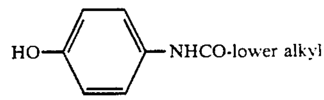

with compounds of formula (III) as hereinbefore defined in an organic solvent such as DMSO, DMF, or lower alkylketones in the presence of a base for example alkali metal hydroxides or carbonates at a temperature of 50°-120° C.

Compounds of formula (XXV) are known compounds or may be prepared from known compounds by known methods.

An alternative method for preparing compounds of formula (IC) where W is oxygen, A is N, D is NH and B is C—$CR^3R^4XR^5$ is by cyclisation of a compound of formula (XXVI):

(XXVI)

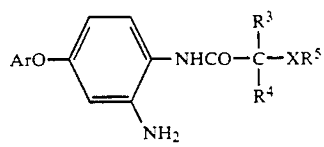

wherein Ar, X, $R^1$, $R^2$ and $R^3$ are as defined in relation to formula (IC) in the presence of a dehydrating agent such as phosphorus pentoxide at 120°-160° C.

Compounds of formula (XXVI) are prepared from compounds of formula (XIX) as hereinbefore defined by reaction with a compound of formula (XXVII):

(XXVII)

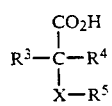

wherein $R^3$, $R^4$, $R^5$ and X are as defined in relation to Formula (IC) in a solvent such as diethyl ether or dichloromethane at 10° to 25° C. in the presence of dicyclohexylcarbodiimide.

Compounds of formula (XXVII) are known compounds or may be produced from known compounds by known methods.

Compounds of formula (IC) where A is N, D is N-lower alkyl and B is C—$CR^3R^4XR^5$ may also be prepared from compounds of formula (XXVIII):

(XXVIII)

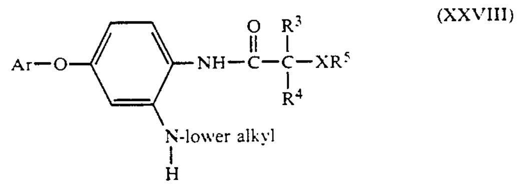

wherein Ar, X, $R^3$, $R^4$ and $R^5$ are as defined in relation to formula (IC) using the procedure described for the preparation of compounds of formula (IC) from compounds of formula (XXVI).

Compounds of formula (XXVIII) are prepared from compounds of formula (XXIX):

(XXIX)

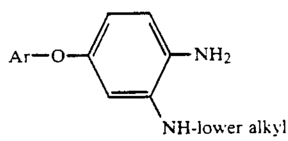

wherein Ar is as defined in relation to formula (IC) using the procedure described for the preparation of compounds of formula (XXVI) from compounds of formula (XIX).

Compounds of formula (XXIX) are prepared by reduction of compounds of formula (XXX):

(XXX)

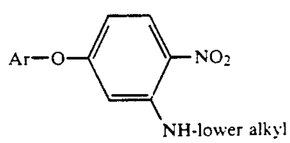

where Ar is as defined in relation to formula (IC) using a wide variety of reducing agents which may be selected from the chemical literature by the skilled worker in the art. The reduction may be carried out for example by using sodium borohydride with a palladium on charcoal catalyst. The reaction is preferably effected in an organic solvent such as a lower alcohol optionally mixed with water at temperatures of from −20° C. to 10° C.

Compounds of formula (XXX) are prepared from compounds of formula (XX) as hereinbefore defined, at 15° to 25° in solvents such as dimethylformamide and lower alkanols by reaction with appropriate lower alkylamines in the presence of a suitable base e.g. triethylamine.

A further embodiment of the invention is represented in the preparation of compounds of formula (IC) where W is —NH— by reaction of compounds of formula (XXXI):

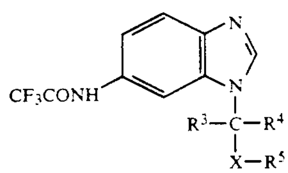

wherein X, $R^3$, $R^4$ and $R^5$ are as defined in relation to formula (IC) with sodium hydride in DMF or DMSO and reacting the anion so formed with a compound of formula (VII) as hereinbefore defined in DMF or DMSO at temperatures from 50° to 90° C.

Compounds of formula (XXXI) can be prepared from compounds of formula (XXXII):

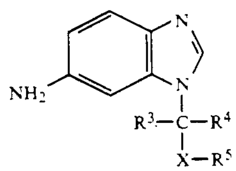

by reaction with trifluoroacetic anhydride according to the procedure described in J. Org. Chem., 1965, 30, 1287.

Compounds of formula (XXXII) are prepared by reduction of the corresponding nitro compound of formula (XXXIII):

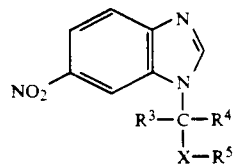

A wide variety of reducing agents may be used and may be selected from the chemical literature by the skilled worker in the art. The reduction may be carried out for example by using sodium dithionite or tin and hydrochloric acid, iron and hydrochloric acid, or hydrogen with a palladium on charcoal catalyst. The reaction is preferably effected in an organic solvent such as a lower alkyl alcohol optionally mixed with water at temperatures of from 20° C. to 90° C.

Compounds of formula (XXXIII) can be prepared from compounds of formula (XXXIV):

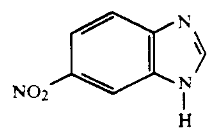

by reaction with compounds of formula (VII) as hereinbefore defined according to the procedure used to prepare compounds of formula (IC) from compound of formula (XVIII).

The compound of formula (XXXIV) is a known compound.

Compounds of formula (IC) where A is N, B is C—$CF_3$, D is $NCR^3R^4XR^5$ and W is O may also be prepared from compounds of formula (XXXV):

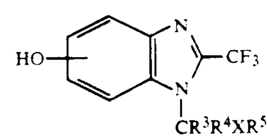

where $R^3$, $R^4$, $R^5$ and X are as defined in relation to formula (IC) by reaction with compounds of formula (III) as hereinbefore defined in an organic solvent such as DMF, DMSO, lower alkyl ketones in the presence of a base such as alkaline metal hydroxides or carbonates at 50°14 120° C.

Compounds of formula (XXXV) are prepared from compounds of formula (XXXVI):

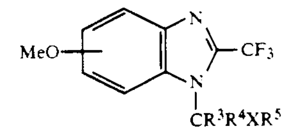

by demethylation using boron tribromide in an organic solvent such as dichloromethane at −70° C. followed by esterification using an alcohol e.g. ethanol and concentrated sulphuric acid at 60°-80° C.

Compounds of formula (XXXV) are novel and as such form a further aspect of the invention.

Compounds of formula (XXXVI) may be prepared from 6-methoxy-2-trifluoromethylbenzimidazole by reaction with compounds of formula (VII) as hereinbefore defined in an organic solvent such as acetonitrile, DMF, lower alkyl ketones in the presence of a base such as alkaline metal hydroxides or carbonates at 50°14 120° C.

6-methoxy-2-trifluoromethylbenzimidazole may be prepared from the known compound 4-methoxy-1,2-phenylene diamine hydrochloride by reaction with trifluoroacetic anhydride in trifluoroacetic acid at 70°-80° C. according to the general method of Organic Synthesis Coll Vol. II p65.

Compounds of formula (XXXVI) are novel and as such form a further aspect of the invention.

Compounds of formula (IC) where B is $CR^6$, W is O and $R^6$ is CN may be prepared from compounds of formula (XXXVII):

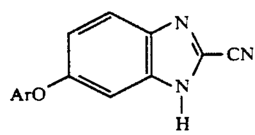

where Ar is as defined in relation to formula (IC) by reaction with a compound of formula (VII) as hereinbefore defined in a suitable solvent e.g. acetonitrile, dimethylsulphoxide, dimethylformamide or a lower alkyl ketone in the presence of an appropriate base e.g. an alkali metal carbonate or hydride at temperature of 70°-100° C. This reaction produces two regio-isomers which may be readily separated by known techniques (e.g. chromatography or preparative tlc) to produce two compounds of formula (IC).

Compounds of formula (XXXVII) may be prepared from compounds of formula (XXXVIII):

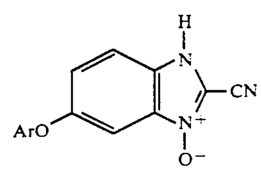

where Ar is as defined in relation to formula (IC) according to the method of S. Takahashi and H. Kano, Chem Pharm. Bull(Tokyo), 1219,14,1966.

Compounds of formula (XXXVII) are novel and as such form a further aspect of the invention.

Compounds of formula (XXXVIII) may be prepared by cyclistation of compounds of formula (XXXIX):

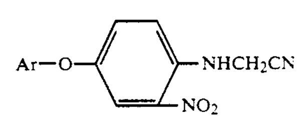

where Ar is as defined in relation to formula (IC) according to the method of D J Moody et al J C S Perkin I, 1988, 681.

Compounds of formula (XXXVIII) are novel and as such form a further aspect of the invention.

Compounds of formula (XXXIX) may be prepared from compounds of formula (XXXX):

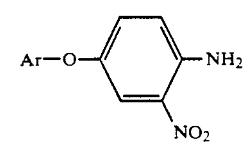

where Ar is as defined in relation formula (IC) by the method of D J Moody et al J C S Perkin I, 1988, 681.

Compounds of formula (XXXIX are novel and as such form a further aspect of the invention.

Compounds of formula (XXXX) may be prepared from compounds of formula (XXIII) as hereinbefore defined by hydrolysis with for example aqueous hydrochloric or sulphuric acid in a lower alcohol e.g. ethanol at 60°-100° C.

If desired one or more of the following steps may be carried out :

i) when $R^5$ is alkoxycarbonyl hydrolysing to the corresponding acid.
ii) when $R^5$ is COOH esterifying or forming a salt, amide, sulphonamide, hydrazide or hydrazinium derivative.
iii) when $R^5$ is an alcohol, oxidation to the corresponding acid or aldehyde.
iv) when $R^5$ is an alkoxycarbonyl, reduction to an alcohol
v) when $R^5$ is an amide, dehydration to the corresponding nitrile.
vi) where A is N formation of a quaternary ammonium salt.
vii) where $R^5$ is an alkoxycarbonyl, n is 0 and one of or both of $R^3$ and $R^4$ are hydrogen, base mediated alkylation to the corresponding substituted ester.

The compounds of formula (I) are active as herbicides and therefore, in a further aspect the invention provides a process for severely damaging or killing unwanted plants which process comprises applying to the plants, or to the growth medium of the plants, an effective amount of a compound of formula (I) as hereinbefore defined.

The compounds of formula (I) are active against a broad range of weed species including monocotyledenous and dicotyledonous species. They may show some selectivity towards certain species; they may be used as selective herbicides in cotton, soya, maize, rice and wheat crops.

The compounds of formula (I) may be applied directly to the plant (post-emergence application) or to the soil before the emergence of the plant (pre-emergence application). They are particularly useful when applied post-emergence.

The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect, the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a waterimmiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic aid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty cids and hexitol anhydrides, for example sorbitan monolaurate; the condensation products of the partial ester with ethylene oxide; and the lecithins; silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogenous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredients(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and suacorite. Bentonite is especially preferred. Other suspending agents include cellulose derivatives and polyvinyl alcohol.

The rate of application of the compounds of the invention of the will depend on a number of factors including, for example, the compound chosen for use, the identity of the plants whose growth is to be inhibited, the formulations selected for use and whether the compound is to be applied for foliage or root uptake. As a general guide, however, an application rate of from 0.01 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity for example herbicide, fungcide, insecticide (optionally with an insecticide synergist) or plant growth regulator. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having complementary action in the particular application.

Examples of useful complementary herbicides include:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalfluralin, pendimethalin, oryzalin;

F. arylurea herbicides such as diuron, flumeturon, metoxuron, neburon, isoproturon, chlorotoluron, chloroxuron, linuron, monolinuron, chlorobromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate molinate, thiobencarb, butylate*, EPTC*, triallate, di-allate, esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxyidim, tralkoxydim, and clethodim;

U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate and bialaphos;

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac, dithiopyr and mefanacet;

BB. Examples of useful contact herbicides include bipyridylium herbicides such as those in which the active entity is paraquat and those in which the active entity is diquat;

* These compounds are preferably employed in combination with a safener such as dichlormid.

The following Examples illustrate the invention:

EXAMPLE 1

This Example illustrates the preparation of compound in Table I.

Step A

6-Nitroindazole (10 g) was dissolved in dry DMF (200cm3) and 50% sodium hydride (2.94 g) added portionwise with stirring. After 20 minutes ethyl 2-bromopropionate ($8cm^3$) was added and the mixture stirred at room temperature for 4 hours, poured into water (1L) and extracted with ethyl acetate four times. The combined organic extracts were washed with water, dried ($MgSO_4$), filtered and the filtrate concentrated under vacuum. The residue was purified by chromatography ($SiO_2$; hexane: t-butylmethyl ether, 7:3) to give ethyl 2-(6-nitroindazol-1-yl)propionate (1.3 g) m.p. 99.7°-100.1° C.; $M^+=263$;

NMR($CDCl_3$): 1.21(t)3H; 2.0(d)3H; 4.2(q)2H; 5.41(q)1H; 7.25(s)1H; 7.85(d)1H; 8.05(d)1H; 8.19(s)1H; 8.4(s)1H.

Step B

Ethyl 2-(6-nitroindazol-1-yl)propionate (1 g), water ($3.7cm^3$) and reduced iron (2.3 g) were stirred in isopropanol ($17cm^3$) at room temperature. Concentrated hydrochloric acid ($0.14cm^3$) was added and the mixture stirred and heated under reflux for 20 minutes. The mixture was filtered through hyflo whilst hot and filter pad washed with ethanol. The combined filtrate was concentrated under vacuum and the residue purified by chromatography ($SiO_2$; $CHCl_3$: ether, 3:1) to give ethyl 2-(6 aminoindazol-1-yl)propionate (0.649). $M^+=233$ NMR($CDCl_3$): 1.19(t)3H; 1.88(d)3H; 3.88(s)2H; 4.16(q)2H; 5.18(q)1H; 6.52(s)1H; 6.58(dd)1H; 7.49(d)1H; 7.97(s)1H.

Step C

Ethyl 2-(6-aminoindazol-1-yl)propionate (0.49 g) was stirred with hot 35% sulphuric acid ($2.12cm^3$), ice (2.12 g) added and the mixture cooled in an ice/salt bath. Sodium nitrite (0.187 g) in water ($2cm^3$) was added dropwise at 0° C. The mixture was stirred for 5 minutes at 0° C. and a few crystals of urea added. Hydrated copper (II) nitrate (8 g) in water ($74cm^3$) was then added followed by copper (I) oxide (0.3 g) and the mixture stirred for 15 minutes at 0° C. and 1.5 hours at hours at room temperature. The reaction mixture was extracted with ethyl acetate four times, the combined organic extracts washed with water, dried ($MgSO_4$), filtered and the filtrate concentrated under vacuum. The residue was purified by chromatography ($SiO_2$, diethyl ether; then hexane: diethyl ether, 35:65) to give ethyl 2-(6-hydroxyindazol-1-yl)propionate (30 mgs)

NMR($CDCl_3$) 1.16(t)3H; 1.88(d)3H; 4.14(q)2H; 5.20(q)1H; 6.67(s)1H; 6.76(m)2H; 7.55(d)1H; 7.95(s)1H.

Step D

Ethyl 2-(6-hydroxyindazol-1-yl)propionate (30 mgs) was dissolved in 0.72 $cm^3$ of a mixture of dry methyl isobutyl ketone ($6cm^3$) and 1 drop of dry DMF. 3-chloro-4,5-difluorobenzotrifluoride (42 mg) and dry potassium carbonate (27mg) were added. The mixture was stirred and heated under reflux for 7 hours, additional dry potassium carbonate being added after 3 hours. After cooling, the solvents were removed under vacuum and diethyl ether added to the residue, the mixture filtered and the inorganic portion washed thoroughly with diethyl ether. The combined ethereal filtrate was concentrated under vacuum and the residue purified by chromatography ($SiO_2$; hexane:t-butylmethylether.4:1) to give compound 1, ethyl 2-[6-(2-chloro-4-trifluoromethyl-6-fluorophenoxy) indazol-1-yl]propionate (29 mg). $M^+=430$.

EXAMPLE 2

This Example illustrates the preparation of compound 1 in Table I and compound 33 in Table II.

Step A

3-Chloro-4,5-difluorobenzotrifluoride (99 g) was dissolved in dry MBIK (100 $cm^3$) and 25 drops of dry DMF and dry potassium carbonate (48 g) added. The mixture was stirred and brought to reflux when a solution of 4-methyl-3-nitrophenol (35 g) in dry MIBK (70 $cm^3$) was added over 1 hour. When the addition was complete stirring and reflux were continued for 2 hours. The solvent was removed from the reaction mixture under vacuum and the residue triturated with water ($500 cm^3$). The solid obtained was filtered off, washed with water and air dried. The crude solid was recrystallised from ethanol to give 4-(2-chloro-6-fluoro-4-trifluoromethylphenoxy)-2-nitrotoluene (73.5 g) as an off white solid, m.p. 112.8°-115.4° C.

Step B 4-(2-Chloro-6-fluoro-4-trifluoromethylphenoxy)-2-nitrotoluene (5.57 g) and reduced iron powder (9.7 g) were suspended in isopropanol (73 $cm^3$) and water (16 $cm^3$) and concentrated hydrochloric acid (0.83 $cm^3$) added. The mixture was stirred under reflux for 7 hours, cooled slightly and filtered through Hyflo. The filter pad was washed through with hot ethanol. The combined filtrate was evaporated to dryness, dissolved in ethyl acetate and washed with brine. The organic phase was dried ($MgSO_4$), filtered and the filtrate evaporated to dryness to give a brown oil which was purified by flash chromatography ($CHCl_3$) to give 4-(2-chloro-6-fluoro-4-trifluoromethylphenoxy)-2-aminotoluene (4 g) as a pale brown oil. $M^+ = 320$ NMR($CDCl_3$): δ2.1(s)3H: 3.55-3.70(s)2H; 6.18(dd)1H; 6.21(d)1H, 6.93(d)1H; 7.36(dd)1H; 7.56(s)1H.

Step C 4-(2-Chloro-6-fluoro-4-trifluoromethylphenoxy)-2-amimo toluene (3.66 g) was dissolved in toluene (34 $cm^3$) and anhydrous potassium acetate (1.14 g) and acetic anhydride (3.54 g) added. The mixture was stirred and heated under reflux for 30 minutes. The heating was decreased and isoamylnitrite (2.04 g) added dropwise over 20 minutes at 90° C. After the addition was complete, stirring and heating was continued for a further 3 hours, when the mixture was cooled and shaken with water (100 $cm^3$) in a separating funnel. The organic phase was separated and the aqueous phase extracted twice with ethyl acetate. The combined organic phase was washed with water, dried ($MgSO_4$) filtered and the filtrate evaporated under reduced pressure to yield a brown oil which was purified by flash chromatography ($CHCl_3$:hexane; 9:1) to yield 1-acetyl-6-(2-chloro-6-fluoro-4-trifluoromethylphenoxy) indazole (2.32 g) as a light brown oil. $M^+ = 372$ NMR($CDCl_3$) δ2.74(s)3H; 7.09(dd)1H; 7.42(dd)1H; 7.61(s)1H; 7.7(d)1H; 7.85(s)1H; 8.09(s)1H.

Step D

1-Acetyl-6-(2-chloro-6-fluoro-4-trifluoromethylphenoxy) indazole (2.05 g) was stirred and heated under reflux with methanol (10 $cm^3$) and concentrated hydrochloric acid (6 $cm^3$) for 2 hours and then left to stand at room temperature for 48 hours. The solvent was removed under vacuum and the residue partitioned between ethyl acetate and saturated sodium bicarbonate. The organic phase was washed with water, dried ($MgSO_4$), filtered and the solvent removed from the filtrate under vacuum. The residue, a brown oil, was purified by flash chromatography ($CHCl_3$:ethyl acetate-85:15) to yield 6-(2-chloro-6-fluoro-4-trifluoromethylphenoxy)indazole (1.32 g) as a straw colored oil which solidified on standing. m.p. = 133.9°-143.1° C. $M^+ = 330$.

NMR($CDCl_3$); δ6.82(s)1H; 6.93(dd)1H; 7.42(dd)1H; 7.61(s)1H; 7.71(d)1H; 8.04(s)1H; 10.1-14 10.4(s)1H.

Step E 6-(2-Chloro-6-fluoro-4-trifluoromethylphenoxy)indazole (0.7 g) was dissolved in dry DMF (1.5 $cm^3$) and cooled in a waterbath when 50% sodium hydride (0.1 g) was added portionwise with stirring. The mixture was stirred for 10 minutes and ethyl 2-bromopropionate (0.42 g) was added. The mixture was stirred with water cooling for 5 minutes and then at room temperature for 8.5 hours. The reaction was poured into water (15$cm^3$) containing 2M hydrochloric acid (1 $cm^3$) and the mixture extracted with ethyl acetate three times. The organic phase was combined, washed with water, dried ($MgSO_4$), filtered, and the solvent removed from the filtrate under vacuum. The residue was purified by flash chromatography (hexane: TBME, 7:3) to give compound 1, ethyl 2-[6-(2-chloro-6-fluoro-4-trifluoromehylphenoxy)indazol-1-yl]propionate (0.51 g) as a colorless oil and compound 33 ethyl 2-[6-(2-chloro-6-fluoro-4-trifluoromethylphenoxy)indazol-2-yl]propionate (0.154 g) as an oil.

Compound Nos 2, 10, 11, 12, 34, 35 and 36 and were prepared by an analogous process using appropriate reactants.

EXAMPLE 3

This Example illustrates the preparation of compound 3 in Table I.

Ethyl 2-[6-(2-chloro-6-fluoro-4-trifluoromethylphenoxy)indazol-1-yl]propionate prepared as described in Example 2 (30 mgs) was dissolved in THF (0.1 $cm^3$) and isopropanol (0.28 $cm^3$). 1.73M sodium hydroxide (0.04 $cm^3$) was added and the mixture stirred at room temperature for 8 hours and left to stand overnight. The solvent was removed under vacuum and the residue dissolved in water (2 $cm^3$). 2M hydrocloric acid (0.035 $cm^3$) was added dropwise with stirring. After 1.5 hours the solid product was filtered off, washed with water and air dried to give 2-[6-(2-chloro-6-fluoro-4-trifluoromethylphenoxy) indazol-1-yl]propionic acid (11 mgs) as a white solid. Compound No 4 was prepared by an analogous process using appropriate reactants.

EXAMPLE 4

This Example illustrates the preparation of compound 5 in Table I.

6-(2-Chloro-6-fluoro-4-trifluoromethylphenoxy)-indazol-1-ylacetic acid prepared as described in Example 3 (0.319 g) was suspended in dry dichloromethane (6 $cm^3$) and methanol (0.04 $cm^3$) and DMAP (10 mg) added. Dicyclohexylcarbodiimide (0.169 g) was added and the mixture stirred at room temperature for 2 hours and left to stand overnight. The mixture was filtered and the solvent removed from the filtrate under vacuum. The residue was purified by flash chromatography (hexane: TMBE,3:2) to yield methyl 2-[6-(2-chloro-6-fluoro-4-trifluoromethylphenoxy)indazol-1-yl]acetate (0.28 g) as an oil which solidified on standing.

Compounds Nos. 51 and 52 were prepared by analogous processes using appropriate reactants.

EXAMPLE 5

This Example illustrates the preparation of compound 9 in Table I.

Step A

Following the method of R. R. Davies (J. C. S.2412,(1955)) ethyl 2-(6-aminoindazol-1-yl) propionate obtained as described in step B of Example 1 (8 g) was added to water (34 $cm^3$) plus concentrated sulphuric acid (3.4 g) contained in an autoclave. The mixture was heated at 170° C. and 110 psi for 11 hours. On cooling the contents of the autoclave were decanted and the autoclave rinsed with water. The crude product was dissolved in 2M NaOH and the solution reacidified to pH6. The precipitated solid (2.25 g) was removed by filtration washed with water and air dried. The aqueous filtrate was extracted with ethyl acetate three times, the combined organic phase dried ($MgSO_4$), filtered, and the solvent removed from the filtrate under vacuum to give a buff solid (2.32 g).

The aqueous residue from the extraction was evaporated and azeotroped (ethanol) to dryness to give a dark brown solid. Each solid fraction was treated with ethanol (50 $cm^3$) saturated with hydrogen chloride for 2 hours. TLC ($CHCl_3$:diethyl ether; 3:1) showed that each had given the same product. The three reactions were combined and the solvent removed under vacuum. The residue was partitioned between ethyl acetate and water and the organic phase washed with water, dried ($MgSO_4$), filtered, and the solvent removed under vacuum to give a black tar which was purified by flash chromatography ($CHCl_3$:diethyl ether, 3:1) to give ethyl 2-(6-hydroxyindazol-1-yl)propionate (4.61 g) as a brown oil $M^+=234$.

NMR($CDCl_3$) δ1.16(t)3H; 1.88(d)3H; 4.14(q)2H; 5.21(q)1H; 6.18(s)1H; 6.74(m)2H; 7.55(d)1H; 7.94(s)1H.

Step B 3-chloro-4-fluorobenzotrifluoride (0.64 g) and ethyl 2-(6-hydroxyindazol-1-yl)propionate (0.5 g) were dissolved in dry DMSO (5 $cm^3$) and dry potassium carbonate (0.44 g) added. The mixture was stirred and heated at 100° C. for 4 hours. The solvent was removed under vacuum, the residue dissolved in ethyl acetate/water, the organic phase separated and washed with brine. The organic phase was dried ($MgSO_4$), filtered and the solvent removed from the filtrate under vacuum. The residue was purified by flash chromatography (hexane: TBME, 7:3) to give ethyl 2-[6-(2-chloro-4-trifluoromethylphenoxy)indazol-1-yl] propionate (0.425 g) as a colorless oil.

Compound No 6, 14, 15, 16, 17, 21, 22, 23 and 38 was prepared by analogous methods using appropriate reactants.

EXAMPLE 6

This Example describes the preparation of compound 37.

2-Fluoro-3-chloro-5-trifluoromethylpyridine (0.64 g) and ethyl 2-(6-hydroxyindazol-1-yl)propionate obtained as described in Example 1 step C (0.5 g) were dissolved in dry MIBK (12$cm^3$) and dry potassium carbonate (0.44 g) and 2 drops of dry DMF added. The mixture was stirred and heated at 100° C. for 6 hours. The solvent was removed under vacuum and the residue dissolved in chloroform and water. The organic phase was separated, dried (phase separating paper) and the solvent removed from the filtrate under vacuum. The residue was purified by flash chromatography (hexane: TBME, 7:3) to give ethyl 2-[6-(3-chloro-5-trifluoromethylpyrid-2-yloxy)indazol-1-yl] propionate (0.58 g) as a colorless oil.

Compound Nos 7 and 8 were prepared by an analogous process using appropriate reactants.

EXAMPLE 7

This Example describes the preparation of compound 31 in Table I

Step A 3-chloro-6-nitroindazole (20 g) was dissolved in dry DMF (180$cm^3$) and the solution cooled to 5° C. 50% sodium hydride (4.86 g) was added portionwise with stirring and cooling between 5° and 10° C. and then for an additional 15 minutes. Ethyl bromoacetate (16.91 g) was added slowly at 5° C., the reaction mixture warming to 30° C. The reaction mixture was then stirred at 20° C. for four hours. Water (lL) was added and the mixture acidified with diluted hydrochloric acid, shaken with ethyl acetate and filtered through hyflo. The organic phase was separated from the filtrate and the aqueous phase extracted (×2) with ethyl acetate. The combined organic phase was washed with water, dried ($MgSO_4$) filtered and the solvent removed from the filtrate under vacuum. The residue was purified by flash chromatography ($SiO_2$; hexane: TBME, 7:3 and then chloroform:ethyl acetate 95:5) to give ethyl 3-chloro-6-nitroindazol-1-ylacetate (16.25 g) as a pale yellow solid m.pt 109.1°-110.3° C.

NMR $CDCl_3$; δ1.29(t)3H; 4.26(q)2H; 5.18(s)2H; 7.84(d)1H; 8.10(dd)1H; 8.30(s)1H.

Step B

Ethyl 3-chloro-6-nitroindazol-1-ylacetate (16.25 g) was dissolved in hot isopropanol (260$cm^3$), stirred and reduced iron powder (35.4 g) added followed by water (57$cm^3$) and concentrated hydrochloric acid (2.1$cm^3$). The mixture was stirred and heated under reflux for 30 minutes and then filtered whilst hot through hyflo. The solvent was removed from the filtrate under vacuum and the residue partitioned between water and chloroform. The organic phase was filtered through phase separating paper and the solvent removed from the filtrate under vacuum to give a pale yellow solid (12.6 g). The crude solid was recrystallised from hexane/ethyl acetate to yield ethyl 6-amino-3-chloroindazol-1-ylacetate (7.42 g) as buff colored crystals m.pt 151.7°-152.2° C.

NMR $CDCl_3$ δ1.24(t)3H; 3.94(s)2H; 4.20(q)2H; 4.91(s)2H; 6.38(s)1H; 6.60(d)1H; 7.42(d)1H.

Step C

Ethyl 6-amino-3-chloroindazol-1-ylacetate (11.5 g) was warmed with 35% sulphuric acid to obtain a solution. Ice (54 g) was added and the solution cooled to −5° C. in an ice/salt bath. A solution of sodium nitrite (4 g) in water (43$cm^3$) was added slowly with stirring and cooling at 0° C. When addition was complete, the mixture was stirred for 15 minutes at 0° C. A pre-cooled solution (5° C.) of cupric nitrate (173 g) in water (1.6L) was added with stirring and cooling at 5° C. Cooper (I) oxide (6.5 g) was added and the mixture stirred at 0° C. for 0.5 hours, after which it was allowed to warm to room temperature for 4.5 hours. The reaction mixture was extracted with ethyl acetate (×4) and the combined organic phase washed with water, dried ($MgSO_4$), filtered and the solvent removed from the filtrate under vacuum. The residue was stirred with ethanol (400$cm^3$) saturated with hydrogen chloride overnight, evaporated under vacuum and then partitioned between water and ethyl acetate. The organic phase was washed with water, dried ($MgSO_4$), filtered and the solvent removed from the filtrate under vacuum. The residue was purified by flash chromatography ($SiO_2$; chloroform:ether,3:2) to give ethyl 3-chloro-6-hydroxyindazol-1-ylacetate (4.34 g) as a brown solid; recrystallised from toluene, m.pt 138°-142° C.

NMR ($CDCl_3$) δ1.25(t)3H; 4.19(q)2H; 4.95(s)2H; 6.05(s)1H; 6.62(s)1H; 6.76(dd)1H; 7.49(d)1H.

Step D

Ethyl 3-chloro-6-hydroxyindazol-1-ylacetate (1.615 g), 3-chloro-4,5-difluorobenzotrifluoride (2.1g), anhydrous potassium carbonate (1.31 g), were stirred and heated under reflux for 3.5 hours in MIBK ($35cm^3$) containing dry DMF (9 drops). After cooling, the solvent was removed from the reaction mixture under vacuum and the residue triturated with ether ($70cm^3$), filtered, and the solvent removed from the filtrate under vacuum. The residue was purified by flash chromatography ($SiO_2$; hexane:TBME, 4:1) to give compound No. 31 ethyl 3-chloro-6-(2-chloro-4-trifluoromethyl-6-fluorophenoxy)indazol-1-ylacetate (1.5 g) as a colorless oil.

Compound Nos. 13, 24, 25, 26, 27, 28, 29, 30, 39, 40, 42, 43, 44, 45, 46, 47, 48, 49, 53, 54 and 55 were prepared by analogous processes using appropriate reactants.

EXAMPLE 8

This Example describes the preparation of compound 32 in Table I.

2-[6-(2-chloro-4-trifluoromethyl-6-fluorophenoxy) indazol-1-yl]propionic acid (0.44 g) (prepared as described in Example 3), dicyclohexylcarbodiimide (0.23 g) and 1,1-dimethylhydrazine (0.066 g) were stirred at room temperature in dry dichloromethane ($5cm^3$) for 4.5 hours. The mixture was filtered and the solvent removed from the filtrate under vacuum. The residue was purified by flash chromatography ($SiO_2$; EtOAc: hexane, 4:1 followed by EtOAc) to give compound 32 2-[6-(2-chloro-4-trifluoromethyl-6-fluorophenoxy)indazol-1-y]propionyl -N,N-dimethyl hydrazide (0.36 g) m.pt 173.5°-174.9° C. $M^+=444$.

EXAMPLE 9

This Example describes the preparation of compound 20 in Table I.

2-[6-(2-chloro-4-trifluoromethyl-6 fluorophenoxy) indazol-1-yl] propionyl-N,N-dimethylhydrazide (0.36 g) (prepared as in Example 8) was dissolved in methanol ($14cm^3$) and methyl iodide ($1.16cm^3$) added with stirring. The mixture was left to stand in a stoppered flask for 18 days at room temperature. The solvent was removed under vacuum and the residue triturated with ether to give compound 20, 2-[6-(2-chloro-4-trifluoromethyl-6-fluorophenoxy)indazol-1-yl]propionyl trimethylhydrazinium iodide (0.369 g) as a pale yellow solid, m.pt 166.8°-167.5° C.

EXAMPLE 10

This Example describes the preparation of compound 19 in Table I.

Ethyl 2-[6-(2-chloro-4-trifluoromethyl-6-flouro-phenoxy)indazol-1-yl]propionate (0.41 g) (prepared as in Example 1) was dissolved in methanol ($25cm^3$), 880 ammonia ($15cm^3$) added and the mixture stirred at room temperature for 18 hours. The white precipitate was collected by filtration and the solvent removed from the filtrate under vacuum. The residue was purified by flash chromatography ($SiO_2$; EtOAc) to give compound 19, 2-[6-(2-chloro-4-trifluoromethyl-6-fluorophenoxy)indazol-1-yl]propionamide as a white solid; total yield=250 mgs. m.pt 171°-172.5 ° C.

EXAMPLE 11

This Example describes the preparation of compound No. 56.

2-[6-(2-chloro-4-trifluoromethyl-6-fluoro(phenoxy)-indazol-1-yl]propionic acid (0.45 g) was suspended in dry 1,2-dichloroethane ($5cm^3$) and thionyl chloride (0.132 g) together with 1,2-dichloroethane($3cm^3$) was added. The mixture was stirred and heated under reflux for 3 hours, cooled and the solvent removed under vacuum. Dry 1,2-dichloroethane ($5cm^3$) was added to the residue, the solution stirred and cooled in iced water, and DMAP (0.136 g) added followed by methane sulphonamide (0.106 g). The mixture was stirred at room temperature overnight when the solvent was removed under vacuum. The residue was purified by flash chromatography ($SiO_2$; chloroform: acetone: glacial acetic acid, 900:67:33) to give 2-[6-(2-chloro-4-trifluoromethyl-6-fluorophenoxy)indazol-1-yl]-N-(methylsulphonyl)propionamide (0.39 g) as a white solid m.pt 175°-177° C.

EXAMPLE 12

This Example illustrates the preparation of compound 61 in Table IV and compound 75 in Table V:

Step A 4-(2-chloro-4-trifluoromethyl-6-fluorophenoxy)-1,2-di aminobenzene (5.65 g) was stirred overnight at room temperature with a mixture of trifluoroacetic acid ($9.6cm^3$) and trifluoroacetic anhydride ($2.6cm^3$). The mixture was then heated under reflux for 2 hours, cooled and added to iced water ($100cm^3$). 2M sodium hydroxide ($71cm^3$) as added with stirring and the mixture shaken with ethyl acetate. Further small additions of 2M sodium hydroxide were added until the mixture changed from deep blue to pink. The aqueous phase was separated and the organic extract washed with water. The organic phase was dried ($MgSO_4$), filtered and the solvent removed from the filtrate under vacuum. The residue was triturated with hexane to give a solid (6.26 g) m.p. 170.2°-171.9° C. A portion was purified by flash chromatography ($SiO_2$; $CHCl_3$: $Et_2O$,96:4) to give 2-trifluoromethyl-6-(2-chloro-4-trifluoromethyl-6- fluorophenoxy)benzimidazole. $M^+=398$.

Step B 2-trifluoromethyl-6-(2-chloro-4-trifluoromethyl-6-fluorophenoxy)benzimidazole (2 g) was dissolved in dry acetonitrile ($10cm^3$) and ethyl 2-bromopropionate (0.93 g) and dry potassium carbonate (1.04 g) added. The mixture was stirred and heated under reflux for 2 hours, cooled and filtered. The filtrate was concentrated under vacuum to give a dark brown oil. The oil was purified by chromatography ($SiO_2$; $CHCl_3$ and then $CHCl_3$ $Et_2O$, 95:5) to give ethyl 2-[2-trifluoromethyl-5-(2-chloro-4-trifluoromethyl-6-fluorophenoxy) benzimidazol-1-yl] propionate, (0.76 g) (compound 61) as the faster component and ethyl 2-[2-trifluoromethyl-6-(2-chloro-4-triflouromethyl-6-fluorophenoxy) benzimidazol-1-yl] propionate, (compound 75) (0.62 g) as the slower component.

EXAMPLE 13

This Example illustrates the preparation of compound 93.

Ethyl 2-[2-trifluoromethyl-6-(2-chloro-4-trifluoromethyl-6-fluorophenoxy) benzimidazol-1-yl] propionate, (0.43 g) was dissolved in dry dichloromethane (1.4cm$^3$) and 1M triethyloxonium tetrafluoroborate in dichloromethane solution (0.86cm$^3$) was added with stirring. The reaction mixture was left to stir at room temperature for 7 days when the solvent was removed under vacuum. The residue was triturated with ether and the solid collected, washed with ether and dried to give ethyl 2-[6-(2-chloro-6-fluoro-4-trifluoromethyl-phenoxy)-3-ethyl-2-trifluoromethyl benzimidazolium-1-yl] propionate tetrafluoroborate, compound 93 (0.227 g), m.p. 135°-136.1° C.

Compound 92 in Table IV was prepared in a similar manner using appropriate reactants.

EXAMPLE 14

This Example describes the preparation of compound 95.

Step A 4-(2-chloro-4-trifluoromethyl-6-fluorophenoxy)-1,2-diaminobenzene (1.04 g), monoethyl 2-methylmalonate (473 mg) and DMAP (20 mg) were dissolved in stirred, ice-cooled dry dichloromethane (20cm$^3$) and dicyclohexylcarbodiimide (690 mgs) added. The mixture was stirred at room temperature for 24 hours, filtered and the filtrate concentrated under vacuum. The residue was purified by column chromatography ($SiO_2$, hexane: EtoAc, 3:2) to give ethyl 2-[2-amino-4-(2-chloro-4-trifluoromethyl-6-fluorophenoxy)phenyl-carbamoyl] propionate, (0.58 g) $M^+ = 448$.

NMR($CDCl_3$): δ1.3(t)3H; 1.55(d)3H; 3.48(q)1H; 3.9(br.s)1H; 4.25(q)2H; 6.25(dd)1H; 6.32(d)1H; 7.1(d)1H; 7.93(dd)1H; 7.58(s)1H; 8.12(br.s)1H.

Step B

Ethyl-[2-amino-4-(2-chloro-4-trifluoromethyl-6-fluorophenoxy)phenylcarbamoyl] propionate (0.4 g) and phosphorus pentoxide (0.5 g) were heated at 140°-160° C. for 2 hours. On cooling water was added followed by sodium carbonate to bring the pH to 4-5. The beige precipitate was collected, air dried, dissolved in methanol and treated with decolorizing charcoal. The filtrate was concentrated under vacuum to give ethyl 2-[6-(2-chloro-4-trifluoromethyl-6-fluorophenoxy)benzimidazol-2-yl] propionate, compound 95, (0.33 g) as a pale brown glass.

EXAMPLE 15

This Example describes the preparation of compound 94.

Step A

Triethylamine (1.64cm$^3$) in DMF (4cm$^3$) was added to a stirred solution of 4-(2-chloro-4-trifluoromethyl-6-fluorophenoxy)-1,2-dinitrobenzene (2.24 g) and methylamine hydrochloride (0.45 g) in dry DMF (6cm$^3$) at room temperature. Stirring was continued for 2.5 days. The mixture was added to brine, acidified and extracted with ethyl acetate. The organic extract was washed with brine, dried ($MgSO_4$), filtered and the filtrate concentrated under vacuum to give 2.39 of a bright yellow oil. The oil was purified using column chromatography ($SiO_2$; hexane: diethyl ether, 9:1) to give 4-(2-chloro-4-trifluoromethyl-6-fluorophenoxy)-2-methylamine-1-nitrobenzene (0.71 g) $M^+ = 364$.

NMR($CDCl_3$): δ2.88(d)3H; 6.0(dd)1H; 6.24(d)1H; 7.38(dd)1H; 7.54(s)1H; 8.1(d+br.s)2H.

Step B

5% palladium on charcoal (0.12 g) was added to stirred, ice cooled methanol (15cm$^3$) under nitrogen purge whilst sodium borohydride (0.25 g) in water (7cm$^3$) was added dropwise. At 2° to 5°, 4-(2-chloro-1-trifluoromethyl-6-fluorophenoxy)-2-methylamino-1-nitrobenzene (0.81 g) in methanol (80cm$^3$) was added dropwise over 20 minutes; the mixture was then stirred to room temperature over 2 hours. The mixture was filtered (hyflo) and the bulk of the filtrate evaporated under vacuum. Water was added to the residue and the aqueous mixture extracted with chloroform. The combined chloroform extracts were filtered (phase separating paper) and the filtrate evaporated under vacuum. The crude product was purified by column chromatography ($SiO_2$, hexane:EtoAc, 3:2) to give 4-(2-chloro-4-trifluoromethyl-6-fluorophenoxy)-2-methylaminoaniline (0.48 g) as an oil.

NMR ($CDCl_3$): δ2.84(s)3H; 6.0(dd)1H; 6.39(d)1H; 6.6(d)1H; 7.37(dd)1H; 7.58(s)1H.

Step C 4-(2-chloro-4-trifluoromethyl-6-fluorophenoxy)-2-methylaminoaniline (0.48 g), monoethyl 2-methylmalonate (0.38 g), DMAP (20 mgs) were dissolved in stirred, dry dichloromethane (5cm$^3$). The mixture was cooled with cold water, dicyclohexylcarbodiimide (0.34 g) added, and left overnight at room temperature. The mixture was filtered (hyflo) and the filtrate concentrated under vacuum. The residue was purified using preparative plates ($SiO_2$, $CH_2C_{12}$ diethyl ether, 9:1) to give ethyl 2-[2-methylamino-4-(2-chloro-4-trifluoromethyl-6-fluorophenoxy)phenylcarbamoyl] propionate (0.38 g) as a white solid.

NMR($CDCl_3$) δ1.3(t); 1.55(d); 2.82(s)3H; 3.48(q)1H; 4.25(q+br.s)3H; 6.05(dd)1H; 7.08(d)1H; 7.39(dd)1H; 7.58(s)1H; 7.86(s)1H.

Step D

Ethyl 2-[2-methylamino-4-(2-chloro-4-triflurometh-yl-6-fluorophenoxy)phenylcarbamoyl] propionate (0.36 g) and phosphorus pentoxide (0.5 g) were heated together at 140°-160° C. for 2 hours. After cooling water was added followed by sodium carbonate to bring the pH to 5-6. Brine was added and the aqueous mixture extracted with ethyl acetate. The combined organic extracts were washed with brine, dried ($MgSO_4$), filtered and the filtrate concentrated under vacuum. The residue was purified by preparative plate chromatography ($SiO_2$; $CH_2C_{12}$ diethyl ether, 85:15) to give ethyl 2-[1-methyl-6-(2-chloro-4-trifluoromethyl-6-fluorophenoxy)benzimidazol-2-yl] propionate, compound 94, (0.19 g) as a pale yellow solid m.p. 123.2°-128.6° C.

EXAMPLE 16

This Example describes the preparation of compound 69 in Table IV and compound 84 in Table V.

Step A 4-methoxy-1,2-phenylenediamine hydrochloride (35 g) was dissolved in trifluoroacetic acid (100 cm$^3$) and trifluoroacetic anhydride (28cm$^3$) added slowly to the stirred solution. The mixture was heated at reflux for 2 hours, cooled to room temperature overnight and made basic with 6 m sodium hydroxide whilst cooling with ice. The aqueous mixture was extracted with ethyl acetate (×3), and the combined organic phase washed with brine, then water treated with decolorizing charcoal and dried ($MgSO_4$). After filtration, evaporation under reduced pressure gave an orange brown solid (14.4 g) which was triturated with petrol, filtered off and air dried to give 6-methoxy-2-trifluoromethylbenzimidazole (14.02 g) as a buff colored solid.

NMR($CDCl_3$): δ3.85(s)3H; 7.05(dd)1H; 7.1(dd)1H; 7.6(d)1H.

Step B 6 methoxy-2-triflurometh ylbenzimidazole (14 g) and ethyl bromoacetate (11.94 g) were dissolved in dry acetonitrile ($200cm^3$). Anhydrous potassium carborate (15 g) was added and the mixture stirred and heated under reflux for 2.5 hours and left to cool overnight to room temperature. The reaction mixture was filtered and the solvent removed from the filtrate under reduced pressure to give a mixture of ethyl 5- and 6-methoxy-2-trifluoromethylbenzimidazol-yl acetate (19.9 g) as a thick orange/brown oil which solified on standing.

NMR ($CDCl_3$) δ1.25(m)6H ($2xCH_3$); 3.88(d)6H ($2xOCH_3$); 4.25 (m)4H($2xCH_2$); 5.5(d)4H($2xCH_2$); 6.72(d)1H; 7.02(dd)1H; 7.1(dd)1H; 7.25(d)1H; 7.32(d)1H;7.7(d)1H

Step C

A mixture of ethyl 5-and 6-methoxy-2-triflurometh yl-benzimidazol-1-yl acetate (6 g from step 2) was dissolved in dry dichloromethane ($100cm^3$) under nitrogen and cooled to −70° C. Boron tribromide (25 g) dissolved in dry dichloromethane ($10cm^3$) was added dropwise with stirring at −70° C., producing a fine brown precipitate. After the addition was complete, the mixture was stirred at room temperature for 3 hours. It was then cooled at 0° C. and ethanol ($45cm^3$) added dropwise keeping the temperature below 5° C. On completion, the mixture was stirred at room temperature overnight and then the solvents removed under vacuum. Ethanol ($100cm^3$) was added to the residue, followed by concentrated sulphuric acid and the solution heated under reflux for 1.5 hours, cooled and the solvent removed under vacuum. Water ($100cm^3$) was added and the mixture made basic with ammonia solution and extracted (×3) with ethyl acetate. The combined organic phase was washed with water, dried ($MgSO_4$), filtered and the solvent removed from the filtrate under vacuum to give a mixture of ethyl 5- and 6-hydroxy-2-trifluoromethylbenzimidazol-1-yl acetate (4.25 g) as a creamy brown solid.

NMR ($CDCl_3$): δ1.25(m)6H ($2xCH_3$); 4.2(m)4H ($2xCH_2$); 4.9(s)2H; 5.0(s)2H; 6.75 (d)1H; 6.9(dd)1H; 7.02(dd)1H; 7.2 m(2H); 7.6(d)1H; 7.9 to 8.6(broad)1H.

Step D

A mixture of ethyl 5- and 6-hydroxy-2-trifluoromethyl-benzimidazol-1-yl acetate (4.25 g from step C), 3-chloro-4, 5-difluorobenzotrifluoride (3.57 g) and anhydrous potassium carbonate (8 g) were stirred and heated at 100° C. for 4 hours in DMF ($200cm^3$). The reaction was cooled and poured into water acidified with dilute hydrochloric acid and extracted with ethyl acetate (×3). The combined organic phase was washed with water, dried ($MgSO_4$), filtered and the solvent removed from the filtrate under vacuum to yield an orange brown oil (7.24 g) which partially solidified on standing. A portion of this (5.26 g) was purified by preparative plate chlorograph (silica; $CH_2Cl_2$) to yield ethyl 5-(2-chloro-6-fluoro-4-trifluoromethyl-phenoxy)-2-trifluoromethylbenzimidazol-1-y 1-acetate(1.7 g), m.p. 77.2°-79.2° C. as the faster component and ethyl 6-(2-chloro-6-fluoro-4-trifluoromethylphenoxy)-2-trifluoromethylbenzimidazol-1-yl acetate(2.83 g m.p. 12.2-113.2) as the slower component.

Compound Nos 64, 65, 66, 67, 68, 70, 71, 79, 80, 81, 82, 83, 85, 86, 86, 97, 98, 99, 108 and 109 were prepared in an analogous manner using appropriate reactants.

EXAMPLE 17

This Example describes the preparation of Compound No. 87 in Table V.

Ethyl-6-(2-chloro-6-fluoro-4-trifluoromethylphenoxy)-2-trifluoromethylbenzimidazol-1-yl acetate (lg) produced as in Example 16 was dissolved in isopropanol ($50cm^3$). Sodium hydroxide (0.15 g) in water ($5cm^3$) was added and the mixture stirred at room temperature for 1 hour. The mixture was poured into water acidified with dilute hydrochloric acid and extracted with ethyl acetate (×3). The combined organic phase was washed with water, dried ($MgSO_4$) filtered and the solvent removed from the filtrate under reduced pressure to give a buff solid (0.879 g), of which 400 mgs was recrystallised from ether/hexane to give 6-(2-chloro-6-fluoro-4-trifluoro-methylphenoxy)-2-trifluoromethylbenzimidazol-1-yl-acetic acid (290 mgs).

Compound Nos. 72 and 76 were prepared in an analogous manner using appropriate reactants.

EXAMPLE 18

This Example describes the preparation of Compound No. 88 in Table V.

6-(2-chloro-6-fluoro-4-trifluoromethylphenoxy)-2-trifluoromethylbenzimidazol-1-ylacetic acid (0.47 g) was heated at reflux in thionyl chloride ($20cm^3$) for 45 minutes, cooled to room temperature and excess thionyl cloride evaporated under reduced pressure. Dry toluene ($20cm^3$) was added and evaporated under reduced pressure. The resulting residue was dissolved in minimum volume of dry toluene and added, with vigorous stirring, to 880 ammonia ($20cm^3$) to produce a thick cream slurry. Stirring was continued for 0.5 hours. Water ($50cm^3$) was added and the mixture extracted with ethyl acetate (×3). The combined extracts were washed in water, dried ($MgSO_4$) filtered and the solvent removed from the filtrate under reduced pressure to give a cream solid (350 mgs). Recrystalliasion from dichloromethane gave 6-(2-chloro-6-fluoro-4-trifluoromethylphenoxy)-2-trifluoromethylbenzimidazol-1-yl acetamide (195 mgs) as an off white solid.

Compound Nos 73, 74, 89, 90 and 91 were prepared in an analogous manner using appropriate reactants.

EXAMPLE 19

This Example illustrates the preparation of Compound 62 in Table IV and compound No. 77 in Table V.

Step A

3-Chloro-4,5-difluorobenzotrifluoride (10 g), 4-acetamido-phenol (7 g) and anhydrous potassium carbonate (12 g) were stirred and heated at 100° C. for 3 hours in dimethyl sulphoxide ($70cm^3$). After cooling the mixture was poured into water, extracted with ethyl acetate (×3) and the combined organic extracts washed with water. The extract was dried ($MgSO_4$), filtered and the solvent removed under vacuum to yield an off-white solid (17.3 g) which was triturated with hexane and filtered to give 4-(2-chloro-6-fluoro-4-trifluoromethylphenoxy)acetanilide (13.95 g) as an off-white solid.

NMR ($CDCl_3$): δ2.15(s)3H; 6.85(d)2H; 7.3 to 7.5(dd)2H and (m)2H; 7.6(s)1H.

Step B 4-(2-Chloro-6-fluoro-4-trifluoromethylphenoxy)-acetanilide (6 g) was suspended in acetic anhydride ($40cm^3$) stirred and cooled to −10° C. A mixture of concentrated nitric acid (1.63 $cm^3$) in acetic anhydride (6.6 $cm^3$) was added dropwise and the resulting yellow suspension stirred at −10° C. for 45 minutes before allowing to warm to room temperature and stand overnight. The reaction mixture was cooled to −5° C. and concentrated. nitric acid (0.81 $cm^3$) in acetic anhydride (3.3 cm) was added. The mixture was left for 4 days at room temperature and then poured into water and extracted with diethyl ether (×3). The combined ethereal extracts were washed with water, dried ($MgSO_4$), filtered, and the solvent removed under vacuum to give a bright yellow slurry. The slurry was poured into water, reextracted with ether, dried ($MgSO_4$) and evaporated to give a yellow solid which was triturated with ether/-hexane and filtered to give 2-nitro-4-(2-chloro-6-fluoro-4-trifluoromethylphenoxy)-acetanilide (3.13 g) as bright yellow solid, M+=392.

Step C

2-Nitro-4-(2-chloro-6-fluoro-4-trifluoromethylphenoxy) acetanilide (2.9 g) was dissolved in acetone ($60cm^3$) and the solution stirred at 5° C. in an ice bath. $40cm^3$ of a 30% titanium trichloride solution in hydrochloric acid was added dropwise over 30 minutes and the reaction mixture stirred at 5° C. for a further 45 minutes before warming to room temperature overnight. The reaction mixture was poured into water and extracted with diethyl ether (×3). The combined ethereal extracts were washed with water, dried ($MgSO_4$), filtered and the filtrate evaporated under reduced pressure to give a pale yellow solid (1.7 g). This was triturated with a 1:1 petrol/ether mixture and filtered to yield 2-amino-4-(2-chloro-6-fluoro-4-trifluoromethylphenoxy)acetanilide (1.2 g) as a cream solid.

NMR ($CDCl_3$) δ2.2(s),3H; 4.2–3.6(broad)1H; 6.225(dd)1H; 6.3(d)1H; 7.025(d)1H; 7.225(bs)1H; 7.35(dd)1H; 7.55(s)1H.

Step D

2-Amino-4-(2-chloro-6-fluoro-4-trifluoromethylphenoxy)acetanilide (1.2 g) was dissolved in glacial acetic acid (5 $cm^3$) and heated at 100° C. for 1 hour. After cooling the solution was poured into water and the mixture basified with 2M sodium hydroxide. The precipitate was filtered off, washed with water and air dried. The solid was purified by preparative plate chromatography (silica; EtOAc+5% HOAc) to give 2-methyl-6-(2-chloro-6-fluoro-4-trifluoromethylphenoxy)benzimidazole (0.5 g) as a pale brown oil.

NMR ($CDCl_3$): δ2.1(s)3H; δ2.45(s)3H; 6.85(dd)1H; 6.9(d)1H; 7.4(m)2H; 7.6(s)1H.

Step E

2-Methyl-6-(2-chloro-6-fluoro-4-trifluoromethylphenoxy) benzimidazole (0.66 g), ethyl 2-bromopropionate ($0.28cm^3$) and anhydrous potassium carbonate (1 g) were stirred and heated under reflux in MEK overnight. The reaction mixture was cooled, poured into water and extracted with ethyl acetate (×3). The combined organic phase was washed with water, dried ($MgSO_4$), filtered and the solvent removed from the filtrate under vacuum to give a brown oil (0.76 g). The oil was purified using preparative plate chromatography ($SiO_2$, ethyl acetate) to give ethyl 2-[2-methyl-6-(2-chloro-6-fluoro-4-trifluoromethylphenoxy)benzimidazol-1-yl] propionate (compound 77) (110 mgs)as the slower component and ethyl 2-[2-methyl-5-(2-chloro-6-fluoro-4-trifluoromethylphenoxy) benzimidazol-1-yl] propionate (compound 62) (220 mgs) as the faster component.

Compound Nos 63 and 78 were prepared in an analogous manner using appropriate reactants.

EXAMPLE 20

This Example illustrates the preparation of compound 100 in Table I and compound 101 in Table V.

Step A 4-(2-chloro-4-trifluoromethyl-6-fluorophenoxy)-2-nitroacetanilide 4.8 g) was heated under reflux for 2 hours in ethanol ($200cm^3$) and concentrated hydrochloric acid ($4cm^3$). The solution was cooled and the solvent removed under vacuum to yield an orange solid which was dissolved in ethyl acetate, washed in the water, dried ($MgSO_4$) and filtered. Evaporation of the filtrate under vacuum gave 4-(2-chloro-4-trifluoromethyl-6-fluorophenoxy)-2-nitroaniline (4.05 g) as an orange solid.

NMR ($CDCl_3$): β7.6(s)1H; 7.5(d)1H; 7.4(dd)1H; 7.2(dd)1H; 6.85(d)1H; 6.0(bs)2H.

Step B

Glacial acetic acid ($40cm^3$) containing concentrated sulphuric acid (3 drops) was added to a stirred mixture of 4-(2-chloro-4-trifluoromethyl-6-fluorophenoxy)-2-nitroaniline (1 g), paraformaldehyde (0.26 g), anhydrous zinc chloride (1.43 g) and potassium cyanide (0.56 g). The resulting suspension was heated at 50°–55° C. for 7.5 hours and left to stand at room temperature overnight. The mixture was poured into water and extracted with ethyl acetate (×2). The combined organic phase was washed with water, dried ($MgSO_4$), and filtered. The solvent was removed from the filtrate under vacuum to give 4-(2-chloro-4-trifluoromethyl-6-fluorophenoxy)-2-nitro-N-cyanomethylaniline (0.82 g) as an orange solid. M+=389.

NMR ($CDCl_3$) δ8.0(b)1H; 7.7(d)1H; 7.6(s 1H; 7.4(dd)2H; 7.0(d)1H; 4.3(d)2H.

Step C 4-(2-chloro-4-trifluoromethyl-6-fluorophenoxy)-2-nitro-N-cyanomethylaniline (1 g) was suspended in hot ethanol ($50cm^3$) and anhydrous potassium carbonate (0.18 g) added. The mixture was then stirred under reflux for 4 hours and left at room temperature overnight. The solvent was evaporated from the mixture under vacuum and the residue dissolved in water ($75cm^3$), filtered and acidified with 2M hydrochloric acid. The yellow precipitate was collected and washed with water, then hexane and air dried to give 2-cyano-5-(2-chloro-4-trifluoromethyl-6-fluorophenoxy)-1H-benzimidazole-3-oxide (0.8 g). $M^+=370$.

Step D 2-cyano-5-(2-chloro-4-trifluoromethyl-6-fluorophenoxy)-1H-benzimidazole-3-oxide (0.8 g) was suspended in chloroform ($5cm^3$) stirred and cooled to 5° C. in an ice bath. Phosphorus trichloride (0.25cm ) was added dropwise and when addition was complete the mixture was heated under reflux for 5 minutes. The resulting solution was cooled, water ($10cm^3$) added slowly and the mixture made basic with aqueous ammonia. The organic layer was separated and the aqueous layer extracted twice with chloroform. The combined organic phase was washed with water, dried ($MgSO_4$), filtered and the filtrate evaporated under vacuum. A portion of the residue was purified by preparative plate chromatogrpahy ($SiO_2$; ether) to give 2-cyano-5-(2-chloro-4-trifluormethyl-6-fluorophenoxy)benzimidazole as a pale yellow solid, recrystallised from ether/hexane. MS (positive FAB) $MH^+=356$.

NMR: δ7.8–7.6(b)1H; 7.6(s)1H; 7.4(dd)1H; 7.2–6.8(bm)2H; 13.8–13.1(bs)1H.

Step E

2-Cyano-5-(2-chloro-4-trifluoromethyl-6-fluorophenoxy)benzimidazole (0.325 g), ethyl 2-bromopropionate ($0.13cm^3$) and anhydrous potassium carbonate (1 g) were heated under reflux in acetonitrile ($30cm^3$) for 2 hours and left at room temperature overnight. The mixture was filtered and the solvent removed from the filtrate under vacuum. The residue was purified by preparative plate chromatography ($SiO_2$; hexane:ether,1:1) to yield ethyl 2-[2-cyano-6-(2-chloro-4-trifluoromethyl-6-fluorophenoxy)benzimidazol-1-yl]-propionate (0.14 g) as the faster component (compound 101) and ethyl 2-[2-cyano-5-(2-chloro-4-trifluoromethyl-6-fluorophenoxy)benzimidazol-1-yl]propionate (0.15 g) as the slower component (compound 100).

Compound Nos 102, 103, 104, 105, 106 and 107 were prepared in an analogous manner using appropriate reactants.

Biological Data

The herbicidal activity of the compounds was tested as follows:

Each chemical was formulated by dissolving it in an appropriate amount, dependent on the final spray volume, of a solvent/surfactant blend, which comprises 78.2 gm/liter of Tween 20 and 21.8 gm/liter of Span 80 adjusted to 1 liter using methylcyclohexanone. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to $5cm^3$ with water, glass beads were added and this mixture was then shaken to effect dissolution or suspension of the chemical, after which the beads were removed. In all cases, the mixture was then diluted with water to the required spray volume. If sprayed independently, volumes of $25cm^3$ and $30cm^3$ were required for pre-emergence and post-emergence tests respectively; if sprayed together, $45cm^3$ was required. The sprayed aqueous emulsion contains 4% of the initial solvent/surfactant mix and the test chemical at an appropriate concentration.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

In a test carried out to detect pre-emergence herbicidal activity, crop seeds were sown at 2 cm depth (i.e. Sb, Ct, Rp, Ww, Mz, Rc, Sy) and weed seeds at 1 cm depth beneath compost and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

The results of the tests are given in Table VII below.

TABLE VII

| COMPOUND NO. | RATE OF APPLICATION | PRE- OR POST-EMERGENCE APPLICATION | TEST PLANTS (see Table VIII) | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| 1 | Pre | 0.25 | 8 | 9 | 4 | 0 | 0 | 9 | 2 | 9 | 9 | — | 9 | 7 | 9 | 0 | 9 | 0 | — | 0 | 0 | — | 0 | 9 | 0 | 0 | 0 |
| | Post | | 9 | 9 | 9 | 9 | 9 | 8 | 3 | 9 | 9 | 9 | 9 | 9 | 9 | 9 | 9 | — | 9 | 6 | 9 | 8 | 9 | 9 | 8 | 9 | 7 |
| 2 | Pre | 0.25 | 0 | 0 | 0 | 0 | 3 | 0 | 0 | 2 | 9 | — | 9 | 4 | 3 | 2 | 3 | 0 | — | 2 | 2 | — | 0 | 2 | 0 | 0 | 0 |
| | Post | | 9 | 9 | 9 | 9 | 6 | 5 | 5 | 9 | 9 | 9 | 9 | 9 | 9 | 9 | 9 | — | 9 | 8 | 8 | 5 | 9 | 9 | 9 | 9 | 8 |
| 3 | Pre | 1 | 9 | 9 | 5 | 0 | 0 | 7 | 0 | — | — | — | 9 | 9 | 9 | 0 | 7 | 0 | — | 1 | 0 | — | 0 | 9 | 9 | 3 | 0 |
| | Post | 0.25 | 7 | 9 | 9 | 6 | 7 | 5 | 3 | — | 9 | — | 9 | 9 | 9 | 9 | 9 | — | 9 | 3 | 5 | 2 | 8 | 9 | 9 | 9 | 2 |
| 4 | Pre | 0.25 | 4 | 4 | 0 | 0 | 0 | 5 | 0 | — | 9 | — | 7 | 0 | 2 | 0 | 0 | 0 | — | 0 | 0 | — | 0 | 0 | 0 | 0 | 0 |
| | Post | | 9 | 9 | 9 | 7 | 8 | 4 | 2 | 8 | 9 | 7 | 9 | 9 | 9 | 9 | 9 | — | 9 | 2 | 4 | 3 | 4 | 9 | 5 | 7 | 4 |
| 5 | Pre | 0.25 | 4 | 4 | 2 | 0 | 0 | 0 | 0 | — | 8 | — | 8 | 0 | 2 | 0 | 0 | 0 | — | 0 | 0 | — | 2 | 0 | 0 | 2 | 0 |
| | Post | 0.0625 | 9 | 9 | 9 | 8 | 8 | 3 | 3 | 9 | 9 | 9 | 9 | 9 | 9 | 9 | 9 | — | 9 | 3 | 2 | 2 | 6 | 9 | 6 | 7 | 2 |
| 6 | Pre | 0.25 | 0 | 0 | 0 | 0 | 0 | 0 | 0 | 9 | 9 | — | 9 | 0 | 0 | 0 | 9 | 0 | — | 2 | 2 | — | 0 | 0 | 0 | 0 | 0 |
| | Post | 0.0625 | 9 | 9 | 9 | 7 | 5 | 2 | 2 | 9 | 9 | — | 9 | 9 | 9 | 9 | 9 | — | 9 | 4 | 2 | — | 0 | 5 | 4 | 0 | 0 |
| 7 | Pre | 1 | 0 | 0 | 0 | 0 | 0 | 0 | 0 | 0 | 8 | — | 4 | 3 | 0 | 0 | 5 | 0 | — | 0 | 0 | — | 0 | 0 | 0 | 0 | 0 |
| | Post | | 3 | 9 | 5 | 8 | 7 | 6 | 5 | 9 | 9 | — | 9 | 9 | 9 | 9 | 9 | — | 9 | 6 | 8 | — | 9 | 9 | 9 | 9 | 2 |
| 8 | Pre | 1 | 0 | 0 | 0 | 0 | 0 | 0 | 0 | 9 | 9 | — | 8 | 3 | 1 | 0 | 6 | 0 | — | 0 | 0 | — | 0 | 3 | 7 | 0 | 0 |
| | Post | 0.25 | 8 | 9 | 9 | 8 | 9 | 6 | 7 | 9 | 9 | — | 9 | 7 | 9 | 9 | 9 | — | 9 | 5 | 4 | — | 9 | 9 | 9 | 9 | 2 |
| 9 | Pre | 0.25 | 0 | 0 | 0 | 0 | 0 | 0 | 0 | 7 | 7 | — | 7 | 3 | 0 | 0 | 3 | 0 | — | 0 | 2 | — | 0 | 0 | 5 | 0 | 0 |
| | Post | 0.0625 | 6 | 8 | 9 | 6 | 0 | 2 | 2 | 9 | 9 | — | 9 | 9 | 9 | 9 | 9 | — | 9 | 3 | 2 | — | 5 | 7 | 2 | 0 | 1 |
| 10 | Pre | 0.25 | 9 | 9 | 6 | 0 | 0 | 7 | 0 | — | — | — | 9 | 7 | 9 | 0 | 9 | 0 | — | 0 | 0 | — | 0 | 9 | 9 | 0 | 0 |
| | Post | 0.0625 | 9 | 9 | 9 | 7 | 7 | 3 | 3 | — | 9 | — | 9 | 9 | 9 | 9 | 9 | — | 9 | 4 | 2 | 2 | 3 | 9 | 9 | 9 | 2 |
| 11 | Pre | 0.25 | 5 | 5 | 0 | 0 | 2 | 3 | 0 | — | 9 | — | 9 | 5 | 8 | 0 | 9 | 0 | — | 2 | 0 | — | 0 | 9 | — | 2 | 0 |
| | Post | 0.0625 | 9 | 9 | 9 | 8 | 8 | 5 | 4 | — | 9 | — | 9 | 9 | 9 | 9 | 9 | — | 9 | 9 | 3 | 8 | 9 | 8 | 9 | 9 | 6 |
| 12 | Pre | 0.25 | 5 | 8 | 0 | 2 | 0 | 0 | 0 | — | 9 | — | 9 | 7 | 9 | 0 | 9 | 0 | — | 3 | 0 | — | 0 | 9 | — | 3 | 0 |
| | Post | 0.0625 | 8 | 9 | 9 | 5 | 8 | 6 | 4 | — | 9 | — | 9 | 9 | 9 | 9 | 8 | — | 9 | 7 | 4 | 6 | 9 | 8 | 8 | 7 | 6 |
| 13 | Pre | 0.25 | 7 | 9 | 7 | 0 | 0 | 6 | 0 | 9 | 9 | 5 | 9 | 9 | 9 | — | 9 | 0 | — | 4 | 5 | — | 7 | 9 | — | 8 | 0 |
| | Post | | 9 | 9 | 9 | 9 | 3 | — | 7 | — | 9 | — | 9 | 9 | 9 | 9 | 9 | — | 9 | 9 | 9 | 9 | 9 | 9 | — | 9 | 6 |
| 14 | Pre | 1 | 9 | 4 | 2 | 2 | 0 | 4 | 0 | — | 9 | 0 | 9 | 7 | 9 | — | 6 | 0 | — | 2 | 2 | — | 5 | 9 | — | 7 | 0 |
| | Post | 0.25 | 9 | 9 | 9 | 9 | 6 | 5 | 9 | — | 9 | 9 | 9 | 9 | 9 | 9 | 9 | — | 9 | 9 | 9 | 7 | 9 | 9 | 9 | 9 | 4 |
| 15 | Pre | 1 | 4 | 4 | 0 | 0 | 2 | 0 | 0 | — | 9 | 0 | 9 | 2 | 7 | 0 | 6 | 0 | — | 3 | 0 | — | 0 | 5 | 0 | 0 | 0 |
| | Post | 0.25 | 5 | 6 | 9 | 5 | 3 | 2 | 2 | — | 7 | 8 | 9 | 4 | 9 | 9 | 5 | — | 6 | 9 | 2 | 5 | 7 | 9 | 9 | 8 | 2 |
| 16 | Pre | 1 | 6 | 5 | 0 | 0 | 2 | 4 | 2 | — | 9 | 0 | 9 | 6 | 7 | — | 5 | 2 | — | 2 | 2 | — | 5 | 6 | — | 5 | 0 |
| | Post | 0.25 | 9 | 9 | 9 | 9 | 7 | 2 | 5 | — | 9 | 9 | 9 | 9 | 9 | 9 | 9 | — | 9 | 8 | 7 | 8 | 9 | 9 | 9 | 9 | 4 |
| 17 | Pre | 1 | 0 | 2 | 0 | 0 | 3 | 0 | 0 | — | 0 | 0 | 0 | 0 | 0 | 0 | 0 | 0 | — | 2 | 0 | — | 0 | 0 | 0 | 0 | 0 |
| | Post | 0.25 | 2 | 0 | 1 | 0 | 0 | 0 | 0 | — | 0 | 0 | 0 | 0 | 0 | 0 | 0 | — | 0 | 0 | 0 | 0 | 4 | 0 | 3 | 0 | 0 |
| 19 | Pre | 0.25 | 5 | 7 | 0 | 0 | 0 | 0 | 0 | — | 9 | — | 9 | 4 | 9 | 0 | 9 | 0 | — | 0 | 0 | — | 5 | 9 | — | 5 | 0 |
| | Post | | 9 | 9 | 9 | 8 | 9 | 6 | 6 | 9 | 9 | 9 | 9 | 9 | 9 | 9 | 9 | — | 9 | 7 | 6 | 7 | 8 | 9 | 9 | 6 | 6 |
| 33 | Pre | 1 | 0 | 0 | 0 | 0 | 0 | 0 | 0 | 3 | 5 | 8 | 5 | 5 | 0 | 0 | 3 | 0 | — | 0 | 0 | — | 0 | 5 | 7 | 0 | — |
| | Post | | 9 | 9 | 9 | 9 | 8 | — | 2 | — | 9 | 9 | 9 | 9 | 9 | 9 | 9 | — | 9 | 2 | 3 | 3 | 9 | 9 | 9 | 9 | 4 |
| 34 | Pre | 0.25 | 0 | 0 | 0 | 0 | 0 | 0 | 0 | 2 | 0 | — | 3 | 4 | 0 | 2 | 3 | 0 | — | 3 | 0 | — | 0 | 2 | 0 | 0 | 0 |
| | Post | | 5 | 9 | 8 | 4 | 5 | 0 | 0 | 4 | 8 | 9 | 9 | 5 | 9 | 4 | 9 | — | 5 | 0 | 3 | 0 | 3 | 6 | 3 | 0 | 0 |
| 35 | Pre | 1 | 0 | 2 | 2 | 0 | 0 | 0 | 0 | — | — | — | 6 | 0 | 3 | 0 | 0 | 0 | — | 0 | 0 | — | 0 | 0 | 0 | 0 | 0 |
| | Post | 0.25 | 3 | 7 | 9 | 5 | 0 | 2 | 2 | — | 9 | — | 9 | 5 | 9 | 9 | 7 | — | 7 | 2 | 2 | 2 | 2 | 9 | 7 | 0 | 0 |
| 36 | Pre | 1 | 0 | 0 | 0 | 0 | 0 | 0 | 0 | — | — | — | 3 | 3 | 0 | 0 | 0 | 0 | — | 0 | 0 | — | 0 | 0 | 0 | 0 | 0 |
| | Post | | 5 | 9 | 9 | 7 | 9 | 0 | 1 | — | 9 | — | 9 | 5 | 9 | 9 | 5 | — | 2 | 2 | 0 | 0 | 2 | 7 | 8 | 0 | 0 |
| 37 | Pre | 1 | 0 | 0 | 0 | 0 | 0 | 0 | 0 | 8 | 9 | — | 5 | 0 | 5 | 0 | 3 | 0 | — | 0 | 2 | — | 0 | 6 | 0 | 0 | 0 |
| | Post | 0.25 | 7 | 9 | 9 | 7 | 7 | 6 | 7 | 9 | 9 | — | 9 | 7 | 9 | 9 | 9 | — | 9 | 5 | 9 | — | 9 | 9 | 8 | 9 | 1 |
| 61 | Pre | 1 | 0 | 0 | 0 | 0 | 0 | 0 | 0 | 0 | 0 | 0 | 0 | 0 | 0 | 0 | 0 | — | — | 0 | 0 | — | 0 | 0 | 0 | 0 | 0 |
| | Post | | 3 | 2 | 0 | 0 | 2 | 0 | 0 | 0 | 0 | 0 | 0 | 0 | 3 | 0 | 3 | — | 1 | 0 | 0 | 0 | 0 | 0 | 0 | 1 | 0 |
| 62 | Pre | 1 | 0 | 7 | 0 | 0 | 0 | 2 | 0 | 0 | 0 | — | 0 | 0 | 0 | 0 | 0 | 0 | — | 7 | 0 | — | 0 | 0 | 0 | 0 | 0 |
| | Post | | 7 | 9 | 3 | 7 | 9 | 1 | 0 | 7 | 9 | — | 9 | 5 | 9 | 5 | 9 | — | 7 | 5 | 1 | 4 | 9 | 2 | 7 | 6 | — |
| 63 | Pre | 1 | 0 | 0 | 3 | 0 | 0 | 0 | 0 | 0 | 0 | — | 0 | 0 | 0 | 0 | 0 | 0 | — | 0 | 0 | — | 0 | 0 | 0 | 0 | 0 |

TABLE VII-continued

| COMPOUND NO. | RATE OF APPLICATION | PRE- OR POST-EMERGENCE APPLICATION | TEST PLANTS (see Table VIII) Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
|---|---|---|---|---|---|---|---|---|---|---|---|---|---|---|---|---|---|---|---|---|---|---|---|---|---|---|---|
| | Post | | 2 | 2 | 1 | 0 | 2 | 0 | 0 | 0 | 0 | — | 0 | 0 | 7 | 0 | 7 | — | 2 | 9 | 2 | 2 0 | 2 | 2 | 0 | 0 | |
| 64 | Pre | 1 | 0 | 4 | 0 | 0 | 0 | 0 | 0 | 0 | 0 | — | 0 | 0 | 0 | 0 | 0 | 0 | — | 4 | 0 | — | 0 | 2 | 0 | 0 | 0 |
| | Post | | 0 | 0 | 0 | 0 | 2 | 0 | 0 | 0 | 0 | — | 0 | 0 | 0 | 0 | 0 | — | 6 | 0 | 3 | 0 | 0 | 0 | 0 | 0 | 0 |
| 65 | Pre | 1 | 0 | 0 | 0 | 0 | 0 | 4 | 0 | 0 | 0 | — | 0 | 0 | 0 | 0 | 0 | 0 | — | 0 | 0 | — | 0 | 0 | 0 | 0 | 0 |
| | Post | | 0 | 0 | 0 | 0 | 0 | 0 | 0 | 0 | 0 | 0 | 0 | 0 | 5 | 0 | 0 | — | 0 | 0 | 1 | 0 | 0 | 3 | 0 | 0 | 0 |
| 66 | Pre | 1 | 0 | 0 | 1 | 0 | 0 | 0 | 0 | 0 | 0 | — | 0 | 0 | 0 | 0 | 1 | 0 | — | 0 | 0 | — | 0 | 0 | 0 | 0 | 0 |
| | Post | | 2 | 1 | 2 | 3 | 0 | 1 | 0 | 0 | 0 | 0 | 0 | 0 | 0 | 0 | 0 | — | 0 | 0 | 0 | 0 | 0 | 7 | 0 | 0 | 0 |
| 67 | Pre | 1 | 0 | 0 | 0 | 0 | 0 | 0 | 0 | 0 | 0 | — | 0 | 0 | 0 | 0 | 1 | 0 | — | 0 | 0 | — | 0 | 0 | 0 | 0 | 0 |
| | Post | | 0 | 0 | 2 | 3 | 2 | 0 | 0 | 3 | 4 | 0 | 9 | 2 | 5 | 0 | 2 | — | 0 | 0 | 0 | 0 | 0 | 0 | 0 | 0 | 0 |
| 68 | Pre | 1 | 0 | 9 | 0 | 0 | 0 | 0 | 0 | 0 | 0 | — | 0 | 0 | 0 | 0 | 0 | 0 | — | 0 | 0 | — | 0 | 0 | 7 | 0 | 0 |
| | Post | | 4 | 2 | 6 | 5 | 5 | 0 | 6 | 9 | — | 8 | 5 | 9 | 0 | 5 | — | 2 | 4 | 0 | 0 | 5 | 0 | 2 | 0 | 0 | |
| 69 | Pre | 1 | 0 | 6 | 0 | 4 | 0 | 0 | 0 | 0 | 0 | — | 0 | 0 | 0 | 0 | 0 | 0 | — | 0 | 0 | — | 0 | 0 | 0 | 0 | 0 |
| | Post | | 4 | 5 | 0 | 4 | 3 | 0 | 0 | 5 | 9 | — | 9 | 3 | 3 | 0 | 5 | — | 5 | 5 | 0 | 0 | 4 | 0 | 0 | 4 | 0 |
| 70 | Pre | 1 | 0 | 0 | 0 | 0 | 0 | 0 | 0 | — | 5 | — | 4 | 0 | 0 | 0 | 0 | 0 | — | 0 | 0 | — | 0 | 0 | 0 | 0 | 0 |
| | Post | | 0 | 0 | 1 | 0 | 0 | 0 | 0 | — | 0 | — | 0 | 0 | 0 | 0 | 0 | — | 0 | 0 | 0 | 0 | 0 | 0 | 0 | 0 | 0 |
| 71 | Pre | 1 | 0 | 0 | 0 | 0 | 0 | 0 | 0 | 0 | 0 | — | 0 | 0 | 5 | 0 | 0 | 0 | — | 0 | 0 | — | 0 | 9 | 9 | 0 | 0 |
| | Post | | 2 | 0 | 0 | 0 | 7 | 0 | 0 | 3 | 6 | — | 3 | 4 | 6 | 0 | 4 | — | 2 | 3 | 4 | 0 | 4 | 0 | 0 | 0 | 0 |
| 72 | Pre | 1 | 3 | 9 | 0 | 0 | 0 | 3 | 0 | 0 | 0 | — | 0 | 0 | 0 | 0 | 0 | 0 | — | 0 | 0 | — | 0 | 0 | 0 | 0 | 0 |
| | Post | | 5 | 6 | 0 | 6 | 0 | 0 | 0 | 5 | 9 | — | 3 | 3 | 2 | 0 | 0 | — | 0 | 6 | 3 | 0 | 0 | 0 | 0 | 0 | 0 |
| 73 | Pre | 1 | 6 | 9 | 0 | 4 | 0 | 0 | 0 | 0 | 5 | — | 0 | 0 | 0 | 0 | 0 | 0 | — | 0 | 0 | — | 0 | 0 | 8 | 0 | 0 |
| | Post | | 0 | 0 | 0 | 0 | 0 | 0 | 0 | 0 | 0 | — | 0 | 0 | 0 | 0 | 0 | — | 0 | 0 | 0 | 0 | 0 | 0 | 0 | 0 | 0 |
| 74 | Pre | 1 | 5 | 5 | 0 | 0 | 0 | 0 | 0 | 0 | 0 | — | 0 | 0 | 0 | 0 | 0 | 0 | — | 0 | 0 | — | 0 | 0 | 6 | 0 | 0 |
| | Post | | 0 | 0 | 0 | 0 | 0 | 0 | 0 | 0 | 0 | — | 0 | 0 | 0 | 0 | 0 | — | 0 | 0 | 0 | 0 | 4 | 0 | 0 | 0 | 0 |
| 75 | Pre | 1 | 9 | 7 | 0 | 0 | 2 | 0 | 5 | 8 | 9 | 2 | 9 | 7 | 8 | 3 | 9 | — | — | 0 | 0 | — | 7 | 9 | 9 | 7 | 0 |
| | Post | | 9 | 9 | 9 | 5 | 7 | 2 | 0 | 7 | 9 | 7 | 9 | 9 | 9 | 9 | 9 | — | 9 | 3 | 3 | 5 | 8 | 7 | 9 | 8 | 2 |
| 77 | Pre | 1 | 0 | 4 | 0 | 0 | 0 | 0 | 0 | 7 | 8 | — | 7 | 4 | 0 | 0 | 4 | 0 | — | 0 | 0 | — | 0 | 0 | 0 | 0 | 0 |
| | Post | | 6 | 9 | 9 | 6 | 9 | 3 | 6 | 8 | 9 | — | 9 | 9 | 9 | 9 | 9 | — | 9 | 9 | 3 | 5 | 9 | 6 | 8 | 6 | 5 |
| 78 | Pre | 1 | 0 | 0 | 0 | 0 | 0 | 0 | 4 | 0 | 0 | — | 0 | 3 | 0 | 3 | 0 | — | — | 0 | 0 | — | 0 | 0 | 0 | 0 | 0 |
| | Post | | 4 | 6 | 2 | 8 | 7 | 4 | 0 | 6 | 8 | — | 0 | 2 | 9 | 2 | 9 | — | 7 | 7 | 0 | 0 | 6 | 2 | 4 | 7 | 1 |
| 79 | Pre | 1 | 0 | 4 | 3 | 0 | 0 | 0 | 0 | 0 | 0 | — | 0 | 0 | 0 | 3 | 0 | 0 | — | 0 | 0 | — | 3 | 0 | 0 | 0 | 0 |
| | Post | | 1 | 4 | 2 | 0 | 2 | 0 | 0 | 5 | 7 | — | 7 | 1 | 6 | 5 | 7 | — | 4 | 8 | 0 | 2 | 5 | 2 | 5 | 5 | 0 |
| 80 | Pre | 1 | 0 | 0 | 1 | 0 | 0 | 0 | 0 | 0 | 0 | — | 0 | 0 | 0 | 0 | 0 | 0 | — | 0 | 0 | — | 0 | 0 | 0 | 0 | 0 |
| | Post | | 2 | 0 | 4 | 0 | 7 | 0 | 0 | 2 | 6 | 2 | 5 | 0 | 8 | 0 | 2 | — | 0 | 0 | 1 | 0 | 2 | — | 0 | 1 | 0 |
| 81 | Pre | 1 | 0 | 0 | 0 | 0 | 0 | 0 | 0 | 0 | 0 | — | 0 | 0 | 2 | 0 | 0 | 0 | — | 0 | 0 | — | 0 | 0 | 0 | 0 | 0 |
| | Post | | 6 | 9 | 9 | 8 | 7 | 0 | 0 | 9 | 8 | 8 | 9 | 5 | 9 | 9 | 5 | — | 9 | 3 | 1 | 1 | 2 | 6 | 0 | 1 | 0 |
| 82 | Pre | 1 | 0 | 0 | 0 | 0 | 0 | 0 | 6 | 0 | 8 | — | 9 | 0 | 9 | 4 | 6 | 0 | — | 2 | 0 | — | 0 | 9 | 0 | 0 | 0 |
| | Post | | 7 | 9 | 9 | 7 | 6 | 1 | 2 | 9 | 9 | 9 | 9 | 7 | 9 | 9 | 8 | — | 9 | 2 | 2 | 2 | 6 | 9 | 3 | 0 | 0 |
| 83 | Pre | 1 | 0 | 0 | 0 | 0 | 0 | 0 | 0 | — | 0 | — | 0 | 0 | 0 | 0 | 0 | 0 | — | 0 | 0 | — | 0 | 0 | 0 | 0 | 0 |
| | Post | 0.25 | 5 | 8 | 5 | 5 | 5 | 0 | 0 | — | 8 | — | 9 | 3 | 9 | 9 | 6 | — | 3 | 0 | 1 | 3 | 6 | 5 | 0 | 0 | 0 |
| 84 | Pre | 1 | 9 | 7 | 0 | 0 | 0 | 0 | 0 | — | 9 | — | 9 | 7 | 9 | 3 | 9 | 0 | — | 0 | 0 | — | 1 | 9 | — | 1 | 0 |
| | Post | 0.25 | 9 | 9 | 5 | 6 | 7 | 1 | 5 | — | 9 | — | 9 | 9 | 9 | 9 | 9 | — | 9 | 2 | 2 | 4 | 9 | 8 | 3 | 0 | 2 |
| 85 | Pre | 1 | 0 | 0 | 0 | 3 | 0 | 0 | 0 | 0 | 0 | — | 0 | 0 | 6 | 0 | 5 | 0 | — | 0 | 0 | — | 0 | 0 | 2 | 0 | 0 |
| | Post | | 2 | 2 | 3 | 3 | 7 | 0 | 3 | 5 | 8 | — | 9 | 6 | 6 | 0 | 4 | — | 0 | 4 | 3 | 0 | 4 | 0 | 3 | 3 | 0 |
| 86 | Pre | 1 | 0 | 0 | 0 | 0 | 0 | 0 | 0 | — | 9 | — | 9 | 1 | 9 | 0 | 0 | 0 | — | 0 | 0 | 0 | 9 | 0 | 0 | 0 | 0 |
| | Post | | 6 | 8 | 5 | 6 | 7 | 1 | 1 | — | 8 | — | 9 | 9 | 9 | 9 | 7 | — | 9 | 2 | 2 | 2 | 7 | 6 | 0 | 2 | 2 |
| 87 | Pre | 1 | 7 | 6 | 0 | 0 | 0 | 0 | 0 | — | 8 | — | 9 | 3 | 8 | 0 | 5 | 0 | — | 0 | 0 | — | 1 | 0 | 0 | 0 | 0 |
| | Post | | 9 | 9 | 9 | 9 | 9 | 2 | 4 | — | 9 | — | 9 | 9 | 9 | 9 | 9 | — | 9 | 2 | 3 | 3 | 9 | 9 | 9 | 2 | 2 |
| 88 | Pre | 1 | 6 | 7 | 0 | 0 | 0 | 0 | 0 | — | 9 | — | 9 | 2 | 4 | 0 | 5 | 0 | — | 0 | 0 | — | 2 | 0 | — | 0 | 0 |
| | Post | | 6 | 3 | 5 | 4 | 7 | 1 | 1 | — | 7 | — | 9 | 4 | 6 | 0 | 3 | — | 3 | 1 | 0 | 0 | 6 | 5 | 0 | 0 | 0 |
| 89 | Pre | 1 | 1 | 0 | 0 | 0 | 0 | 0 | 0 | — | 9 | — | 9 | 6 | 9 | 0 | 7 | 0 | — | 3 | 0 | — | 0 | 5 | — | 0 | 0 |
| | Post | | 7 | 5 | 5 | 4 | 0 | 0 | 1 | — | 8 | — | 9 | 3 | 4 | 3 | 2 | — | 4 | 1 | 2 | 0 | 6 | 2 | 0 | 0 | 0 |

TABLE VII-continued

| COMPOUND NO. | RATE OF APPLICATION | PRE- OR POST-EMERGENCE APPLICATION | TEST PLANTS (see Table VIII) | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| 90 | 1 | Pre | 0 | 0 | 0 | 0 | 0 | 0 | 0 | — | 9 | — | 9 | 1 | 0 | 0 | 0 | 0 | — | 0 | 0 | — | 0 | 0 | 0 | 0 | 0 |
| | | Post | 5 | 2 | 3 | 3 | 0 | 0 | 0 | — | 7 | — | 9 | 2 | 3 | 0 | 5 | — | 3 | 0 | 0 | 0 | 0 | 0 | 0 | 0 | 0 |
| 92 | 1 | Pre | 0 | 0 | 0 | 0 | 0 | 0 | 0 | 0 | 0 | 0 | 0 | 0 | 0 | 0 | 0 | — | — | 0 | 0 | — | 0 | 0 | 0 | 0 | 0 |
| | | Post | 3 | 0 | 3 | 4 | 4 | 0 | 3 | 0 | 0 | 0 | 9 | 2 | 4 | 0 | 0 | — | 3 | 0 | 0 | 0 | 0 | 0 | 0 | 3 | 0 |
| 93 | 1 | Pre | 9 | 7 | 0 | 0 | 0 | 2 | 0 | 8 | 9 | 2 | 9 | 9 | 9 | 0 | 4 | — | — | 0 | 0 | — | 5 | 9 | 4 | 5 | 0 |
| | | Post | 9 | 9 | 9 | 4 | 4 | 9 | 2 | 9 | 9 | 9 | 9 | 9 | 9 | 9 | 9 | — | 9 | 9 | 9 | 9 | 1 | 3 | 7 | 9 | 4 |
| 94 | 1 | Pre | 4 | 2 | 2 | 3 | 2 | 0 | 0 | 7 | 9 | — | 9 | 6 | 8 | 5 | 0 | — | — | 0 | 0 | — | 0 | 4 | 0 | 0 | 0 |
| | | Post | 8 | 9 | 9 | 5 | 6 | 3 | 4 | 8 | 9 | 9 | 9 | 6 | 2 | 9 | 9 | — | 9 | 3 | 3 | 0 | 5 | 6 | 4 | 5 | 2 |
| 95 | 1 | Pre | 0 | 0 | 3 | 3 | 0 | 0 | 0 | — | 0 | — | 0 | 0 | 0 | 0 | 0 | — | — | 0 | 0 | — | 0 | 0 | 0 | 0 | 0 |
| | | Post | 7 | 6 | 5 | 5 | 1 | 1 | 2 | 7 | 4 | 7 | 6 | 7 | 8 | 3 | — | 3 | 2 | 1 | 2 | 2 | 1 | 2 | 2 | 0 | |
| 96 | 1 | Pre | 0 | 0 | 0 | 0 | 0 | 9 | 0 | 0 | 0 | — | 0 | 0 | 0 | 0 | 2 | 0 | — | 0 | 0 | — | 0 | 0 | — | 0 | 0 |
| | | Post | 0 | 1 | 0 | 0 | 0 | 0 | 0 | 0 | 0 | 0 | 8 | 0 | 0 | 0 | 0 | — | 0 | 0 | 0 | 0 | 0 | 0 | 0 | 0 | 0 |
| 97 | 1 | Pre | 0 | 6 | 0 | 0 | 0 | 0 | 0 | 0 | 0 | — | 0 | 0 | 0 | 0 | 0 | 0 | — | 0 | 0 | — | 0 | 8 | 9 | 8 | 0 |
| | | Post | 0 | 0 | 2 | 0 | 8 | 0 | 3 | — | 0 | 0 | — | 0 | 0 | 0 | 0 | — | 2 | 6 | 8 | 0 | 8 | 4 | 8 | 8 | 2 |
| 98 | 1 | Pre | 0 | 0 | 0 | 0 | 0 | 0 | 0 | 0 | 0 | — | 0 | 0 | 0 | 0 | 0 | 0 | — | 0 | 0 | — | 0 | 0 | — | 0 | 0 |
| | | Post | 6 | 5 | 9 | 4 | 3 | 2 | 0 | 0 | 2 | 0 | 9 | 1 | 8 | 9 | 6 | — | 1 | 0 | 1 | 0 | 1 | 6 | 1 | 6 | 0 |
| 99 | 1 | Pre | 0 | 0 | 0 | 0 | 0 | 5 | 0 | — | 0 | — | 6 | 0 | 2 | 0 | 0 | 0 | — | 0 | 0 | — | 0 | 0 | 0 | 0 | 0 |
| | | Post | 3 | 4 | 1 | 2 | 5 | 0 | 0 | — | 9 | — | 6 | 0 | 1 | 0 | 0 | — | 0 | 0 | 0 | 0 | 0 | 0 | 0 | 0 | 0 |
| 100 | 1 | Pre | 3 | 0 | 2 | — | 0 | — | 2 | — | 0 | — | 2 | — | 2 | — | 2 | 2 | — | — | 2 | — | 2 | 2 | — | 0 | 2 |
| | | Post | 5 | 9 | 8 | 7 | 3 | 1 | 1 | 6 | 9 | 6 | 9 | 3 | 7 | 6 | 7 | — | 5 | 3 | 1 | 0 | 7 | — | 7 | 3 | — |
| 101 | 1 | Pre | 6 | 7 | 0 | — | 0 | — | 0 | — | 9 | — | 9 | 9 | 6 | — | 5 | 2 | — | 2 | 0 | — | 5 | 9 | — | 5 | 2 |
| | | Post | 7 | 9 | 9 | 7 | 9 | 3 | 2 | 9 | 9 | 9 | 9 | 9 | 9 | 9 | 9 | — | 9 | 7 | 5 | 3 | 9 | — | 9 | 8 | — |

TABLE VIII

| Test Plants | |
|---|---|
| Sb | Sugar beet |
| Rp | Rape |
| Ct | Cotton |
| Sy | Soybean |
| Mz | Maize |
| Ww | Winter wheat |
| Rc | Rice |
| Bd | *Bidens pilosa* |
| Ip | *Ipomoea lacunosa* (pre-emergence) *Ipomoea hederacea* (post-emergence) |
| Am | *Amaranthus retroflexus* |
| Pi | *Polygonum aviculare* |
| Ca | *Chenopodium album* |
| Ga | *Galium aparine* |
| Xa | *Xanthium spinosum* |
| Xs | *Xanthium strumarium* |
| Ab | *Abutilon theophrasti* |
| Eh | *Euphorbia heterophylla* |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Ce | *Cyperus esculentes* |

We claim:

1. A compound having the formula

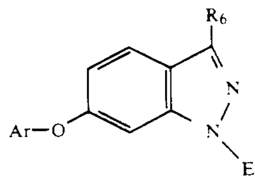

in which:

Ar is an optionally substituted aromatic or heterocyclic ring system;

$R^6$ is H, halogen, $OR^7$, CN, $COOR^8$, alkyl or haloalkyl;

E is $$-C(R^3)(R^4)-XR^5;$$

$R^3$ and $R^4$ are independently selected form H, optionally substituted alkyl, alkenyl or aklynyl, halogen, $NR^9R^{10}$, or $R^3$ and $R^4$ together with the carbon to which they are attached form an optionally substituted alkenyl or cycloalkyl group;

$R^5$ is $CO_2R^{11}$, CN, $COR^{11}$, $CH_2OR^{11}$, $CH(OH)R^{11}$, $CH(OR^{11})R^{12}$, $CSNH_2$, $COSR^{11}$, $CSOR^{11}$, $CONHSO_2R^{11}$, $CONR^{13}R^{14}$, $CONHNR^{13}R^{14}$, $CONHN^+R^{13}R^{14}R^{15}$ $Y^-$, $CO_2^-M^+$ or $COON{=}CR^{13}R^{14}$;

X is $(CH_2)_n$, CH=CH, $CH(OR^{16})CH_2$ or $COCH_2$; where n is 0, 1 or 2;

$M^+$ is an agriculturally acceptable cation;

$Y^-$ is an agriculturally acceptable anion;

$R^7$ and $R^8$ are independently H or lower alkyl;

$R^{11}$, $R^{12}$ and $R^{16}$ are independently selected form H or an optionally substituted alkyl, alkenyl, alkynyl or aryl group;

$R^9$, $R^{10}$, $R^{13}$, $R^{14}$ and $R^{15}$ are independently selected from H or an optionally substituted alkyl, alkenyl, alkenyl, alkynyl or aryl group, providing that the compound is other than 5-(2,4-dichlorophenoxy)-indazol-1-ylacetic acid or its methyl ester;

optional substituents for aryl or heterocyclic rings are up to 5 members selected form halogen; $C_1$-$C_3$ alkyl; $C_1$-$C_{10}$ haloalkyl; $C_1$-$C_{10}$ haloalkoxy; nitro; cyano; $C_1$-$C_3$ alkoxy or $S(O)_pR^a$ where p is 0, 1, or 2 and $R^a$ is $C_1$-$C_{10}$ alkyl; and optional substitutents for alkyl, alkenyl and alkynyl groups are one or more members selected form halogen; nitro, cyano; aryl; $CO_2R^{17}$, $NHCOR^{17}$ or $NHCH_2CO_2R^{17}$ wherein $R^{17}$ is hydrogen, $C_1$-$C_6$ alkyl or an agriculturally acceptable cation; $C_1$-$C_6$ alkoxy; oxo; $S(O)_pR^a$ whre p is 0, 1, or 2 and $R^a$ is $C_1$-$C_{10}$ alkyl; amino; mono or di-($C_1$-$C_6$) alkylamino; $CONR^{18}R^{19}$ wherein $R^{18}$ and $R^{19}$ are independently selected from hydrogen, $C_1$-$C_6$ alkyl, $C_2$-$C_6$ alkenyl or $C_2$-$C_6$ alkynyl.

2. A compound according to claim 1 in which $R^6$ is H or Cl.

3. A compound having the formula

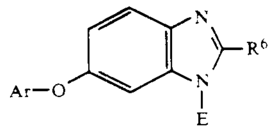

in which:

Ar is an optionally substituted aromatic or heterocyclic ring system;

$R^6$ is H, halogen, $OR^7$, CN, $COOR^8$, alkyl or haloalkyl;

E is $$-C(R^3)(R^4)-XR^5;$$

$R^3$ and $R^4$ are independently selected form H, optionally substituted alkyl, alkenyl or alkynyl, halogen, $NR^9R^{10}$, or $R^3$ and $R^4$ together with the carbon to which they are attached form an optionally substituted alkenyl or cycloalkyl group;

$R^5$ is $CO_2R^{11}$, CN, $COR^{11}$, $CH_2OR^{11}$, $CH(OH)R^{11}$, $CH(OR^{11})R^{12}$, $CSNH_2$, $COSR^{11}$, $CSOR^{11}$, $CONHSO_2R^{11}$, $CONR^{13}R^{14}$, $CONHNR^{13}R^{14}$ $CONHN^+R^{13}R^{14}R^{15}$ $Y^-$, $CO_2^-M^+$ or $COON{=}CR^{13}R^{14}$;

X is $(CH_2)_n$, CH=CH, $CH(OR^{16})CH_2$ or $COCH_2$; where n is 0, 1 or 2;

$M^+$ is an agriculturally acceptable cation;

$Y^-$ is an agriculturally acceptable anion;

$R^7$ and $R^8$ are independently H or lower alkyl;

$R^{11}$, $R^{12}$ and $R^{16}$ are independently selected form H or an optionally substituted alkyl, alkenyl, alkynyl or aryl group;

$R^9$, $R^{10}$, $R^{13}$, $R^{14}$ and $R^{15}$ are independently selected form H or an optionally substituted alkyl, alkenyl, alkynyl or aryl group;

optional substituents for aryl or heterocyclic rings are up to 5 members selected from halogen; $C_1$-$C_3$ alkyl; $C_1$-$C_{10}$ haloalkyl; $C_1$-$C_{10}$ haloalkoxy; nitro; cyano; $C_1$-$C_{10}$ alkoxy or $S(O)_pR^a$ where p is 0, 1, or 2 and $R^a$ is $C_1$-$C_{10}$ alkyl; and optional substituents for alkyl, alkenyl and alkynyl groups are one or more members selected from halogen; nitro, cyano; aryl: $CO_2R^{17}$, $NHCOR^{17}$ or $NHCH_2CO_2R^{17}$ wherein $R^{17}$ is hydrogen, $C_1$-$C_6$ alkyl or an agriculturally acceptable cation; $C_1$-$C_6$ alkoxy; oxo; $S(O)_pR^a$ where p is 0, 1, or 2 and $R^a$ is $C_1$-$C_{10}$ alkyl; amino; mono or di-($C_1$-$C_6$) alkylamino; $CONR^{18}R^{19}$ wherein $R^{18}$ and $R^{19}$ are independently selected form hydrogen, $C_1$-$C_6$ alkyl, $C_2$-$C_6$ alkenyl or $C_2$-$C_6$ alkynyl.

4. A compound according to claim 3 in which $R^6$ is H, $CH_3$, $CF_3$ or CN.

5. A compound according to claim 1 or 3 in which Ar is

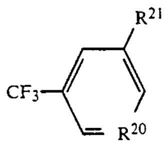

where $R^{20}$ is N, CH or C—$R^{22}$; $R^{21}$ and $R^{22}$ are independently halogen.

6. A compound according to claim 1 or 3 in which E is

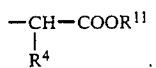

7. A herbicidal composition comprising a herbicidally effective amount of a compound according to claim 1 or 3 in combination with a carrier or diluent.

8. A method of killing or controlling the growth of unwanted plants comprising applying to the plants or to a locus thereof a herbicidally effective amount of a compound according to claim 1 or 3.

* * * * *